United States Patent
Singh et al.

(10) Patent No.: US 12,208,387 B2
(45) Date of Patent: Jan. 28, 2025

(54) APPARATUS AND METHODS FOR SELECTIVE CAPTURE OF MYCOBACTERIA

(71) Applicant: DRIZZLE HEALTH LLC, Baltimore, MD (US)

(72) Inventors: Digvijay Singh, Baltimore, MD (US); Bonolo Mathekga, Baltimore, MD (US); Yukari Manabe, Elkridge, MD (US); Soumyadipta Acharya, Ellicott City, MD (US); Hai Quan Mao, Baltimore, MD (US)

(73) Assignee: Drizzle Health LLC, Baltimore, MD (US)

( * ) Notice: Subject to any disclaimer, the term of this patent is extended or adjusted under 35 U.S.C. 154(b) by 0 days.

(21) Appl. No.: 18/262,375

(22) PCT Filed: Jan. 22, 2022

(86) PCT No.: PCT/US2022/013433
§ 371 (c)(1),
(2) Date: Jul. 20, 2023

(87) PCT Pub. No.: WO2022/159783
PCT Pub. Date: Jul. 28, 2022

(65) Prior Publication Data
US 2024/0042430 A1  Feb. 8, 2024

Related U.S. Application Data

(60) Provisional application No. 63/140,465, filed on Jan. 22, 2021.

(51) Int. Cl.
*B01L 3/00* (2006.01)
*C12N 1/20* (2006.01)
(Continued)

(52) U.S. Cl.
CPC ........ *B01L 3/502707* (2013.01); *C12N 1/205* (2021.05); *C12N 11/08* (2013.01); *B01L 2200/10* (2013.01); *C12R 2001/32* (2021.05)

(58) Field of Classification Search
None
See application file for complete search history.

(56) References Cited

U.S. PATENT DOCUMENTS

| | | |
|---|---|---|
| 8,574,923 B2 | 11/2013 | Cooney et al. |
| 8,603,771 B2 | 12/2013 | Stanley et al. |

(Continued)

OTHER PUBLICATIONS

Grimaldi et al., Plasma functionalization procedure for antibody immobilization for SU-8 based sensor, 2016, Biosensors and Bioelectronics, 86, p. 827-833. (Year: 2016).*

(Continued)

*Primary Examiner* — Lore R Jarrett
(74) *Attorney, Agent, or Firm* — Aurora Consulting LLC; Ashley Sloat; Daniel Wright

(57) ABSTRACT

A device for selectively capturing mycobacteria comprises a substrate and a capture polymer layer of poly-diallyldimethyl ammonium chloride, wherein the capture polymer layer is covalently linked onto the substrate via a UV-initiated polymerization reaction of a solution comprising diallyldimethyl ammonium chloride and a photoinitiator in water purged of dissolved oxygen, and wherein the UV exposure time is 30 seconds to 4 minutes at a power density of about 20 to about 25 mW/cm². A kit can comprise the device. A microfluidic chip comprises at least a portion of at least one channel sidewall coated with a capture polymer layer of poly-diallyldimethyl ammonium chloride. A method for manufacturing the device includes plasma treating a substrate, providing a solution comprising diallyldimethyl ammonium chloride and a photoinitiator in water purged of (Continued)

dissolved oxygen, and coating the plasma-treated substrate via a UV-initiated polymerization reaction.

21 Claims, 15 Drawing Sheets

(51) Int. Cl.
   *C12N 11/08* (2020.01)
   *C12R 1/32* (2006.01)

(56) References Cited

U.S. PATENT DOCUMENTS

| | | | |
|---|---|---|---|
| 10,577,654 B2 | 3/2020 | Grass et al. | |
| 2003/0165428 A1 | 9/2003 | McCombs | |
| 2010/0203521 A1 | 8/2010 | Klapperich et al. | |
| 2015/0203645 A1* | 7/2015 | Rasmussen | B01J 20/3276 427/595 |
| 2015/0321191 A1* | 11/2015 | Kendall | B01J 20/3255 521/149 |
| 2017/0067088 A1* | 3/2017 | O'Brien-Coon | C12Q 1/18 |

OTHER PUBLICATIONS

Lee et al., Inactivation of Mycobacteria by Radicals from Non-Thermal Plasma Jet, 2019, J. Microbiol. Biotechnol., 29(9), p. 1401-1411. (Year: 2019).*

Beaulieu et al., Oxygen Plasma Treatment of Polystyrene and Zeonor: Substrates for Adhesion of Patterned Cells, 2009, American Chemical Society, vol. 25, p. 7169-7176. (Year: 2009).*

Jiang et al., Selective mycobacterial capture with ultraviolet-polymerized polydimethyldiallyl chloride functionalized surfaces, 2024, Journal of Materials Science: Materials in Medicine, 35:57, p. 1-10. (Year: 2024).*

International Search Report re PCT/US2022/013433 dated Apr. 11, 2022 (2 pages).

Written Opinion re PCT/US2022/013433 dated Apr. 11, 2022 (7 pages).

* cited by examiner (not to scale)

pDADMAC grafted on Polystyrene

Polystyrene only $10^3$ cells/mL $10^4$ cells/mL $10^5$ cells/mL

APPARATUS AND METHODS FOR SELECTIVE CAPTURE OF MYCOBACTERIA

CROSS-REFERENCE TO RELATED APPLICATIONS

This application is a 35 U.S.C. 371 National Stage Application of PCT/US2022/013433, filed Jan. 22, 2022, which claims the priority benefit of U.S. Provisional Application No. 63/140,465, filed Jan. 22, 2021, the disclosures of which are herein incorporated by reference in their entireties.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of medical diagnostics, and more specifically to the field of materials and equipment for isolating certain microorganisms.

Described herein are systems and methods for selectively capturing mycobacteria.

BACKGROUND

Tuberculosis (TB) is the leading cause of death amongst all infectious diseases. In 2019, this disease resulted in approximately 1.4 million deaths worldwide. The identification of *Mycobacterium* tuberculosis (MTb) is essential in diagnosing TB. It is estimated that only 56% of all TB cases are bacteriologically confirmed, making underdiagnosis a major contributor to the ongoing TB transmission. Despite having the lowest sensitivity amongst all the diagnostic tests, sputum smear microscopy (SSM) is the most used diagnostic method; it is the cheapest, and trained microscopists are plentiful. It has been reported that approximately 77.6 million smear microscopy tests are performed each year across the top 22 countries with the highest TB burden. With an incidence of 2.7 million, India leads this list.

Approximately 10 million SSM tests were done at the over 20,000 public microscopy centers in India in 2018. These tests cost less than a dollar, and are the most widely used diagnostic test, despite having a sensitivity of only about 50% on average, basically making the test a coin toss. Despite the Indian government's push towards expensive, state of the art molecular diagnostic-based methods such as GeneXpert, there are significant gaps and challenges. India's total budget for TB is about USD 530 Million, and the costs of just testing via these methods are about USD 350 Million over the next 5 years. Further, microbiologically confirmed cases are only about 47% in the public sector, pointing to a huge risk of over-reporting. There is a need for a sensitive low-cost diagnostic test that makes use of existing widespread infrastructure and is widely available and easily distributable.

Fluorescence microscopy (FM) using Auramine O staining for the detection of mycobacteria has been used for decades but has been limited by the mercury vapor lamp (MVL) technology used in conventional FM. Further, FM uses an expensive power supply, is inefficient and short-lived, and has the potential to release toxic mercury. FM, however, is approximately 10% more sensitive than conventional light microscopy (LM) using Ziehl-Neelsen staining. FM also is more efficient because the staining protocol is more efficient, slides can be read at lower magnification and requires a shorter examination time per slide.

Enhancements have been made to the conventional sputum smear microscopy by utilizing light-emitting diodes (LED) for fluorescent microscopy. Although this approach improves sensitivity (5-6% overall), it does not address the root cause of the problem, the minimal capture of MTb from the sample.

MicroSens (Lowell, Mass.) has created magnetic bead technology in an attempt to concentrate the MTb in sputum prior to microscopy. The product adds significant cost to a diagnostic test that otherwise costs cents, and adds more steps and biohazards to the workflow, which requires cumbersome modifications to the infrastructure. Despite advances in microscopy such as LED, the sensitivity of sputum smear microscopy is still limited by the relatively small amount of sputum that can be put on the glass slide, which represents only a fraction of the bacteria in the patient's lungs.

The gold standard for TB diagnosis remains solid or liquid culture. All culture methods require biosafety level 3 (BSL-3) laboratories because the sputum decontamination process includes centrifugation, which increases the risk for aerosol generation. Without BSL-3 facilities, these procedures would pose a significant occupational risk to laboratory personnel. Unfortunately, very few BSL-3 facilities exist in TB high burden countries as they are expensive to build and maintain.

In 2011, the WHO recommended Xpert MTB/RIF (Cepheid, Sunnyvale, Calif.) for diagnosis of pulmonary TB and rifampicin resistance in adults. It is the first rapid molecular test that can be used to simultaneously test for TB and rifampicin resistance, with 98% sensitivity in sputum smear positive patients and sensitivity that ranges from 55-72% in a single sputum from smear-negative patients. Despite its promise as a rapid molecular test, there have been operational challenges, which include the requirement for an ambient temperature of lower than 30° C. (necessitating air conditioning in hot climates), and uninterrupted and stable electrical power supply (requiring generators in several sites). When users were queried, storage space and conditions (28° C.) for cartridges, waste generated (considerably more than for microscopy), and the 12-month shelf-life of cartridges were listed as the main operational challenges. An initial capital investment (machine and computer and approximately $17,000) is required along with on-going maintenance costs.

Accordingly, currently available TB diagnostics that have higher sensitivity than sputum smear microscopy are expensive, require new infrastructure development and their widespread adoption is not expected in the near future.

SUMMARY

There is a need for new and useful system and method for selectively capturing mycobacteria. One aspect of the disclosure herein includes for, in some embodiments, a device for selective capture of mycobacteria comprising: a substrate; and a capture polymer layer of poly-diallyldimethyl ammonium chloride, wherein the capture polymer layer is covalently linked onto the substrate via a UV-initiated polymerization reaction of an aqueous monomer solution comprising: diallyldimethyl ammonium chloride and a photoinitiator in water purged of dissolved oxygen, and wherein the UV exposure time is about 30 seconds to about 4 minutes at a power density of about 20 to about 25 mW/cm². In some embodiments, the UV exposure time is about 50 seconds to about 1 minute and 10 seconds. In other embodiments, the UV exposure time is about 1 minute. In some embodiments, the UV exposure time is about 1 minute and 50 seconds to about 2 minutes and 10 seconds. In other embodiments, the UV exposure time is about 2 minutes. In some embodiments, the UV power density is about 22 mW/cm² to about 24 mW/cm². In other embodiments, the UV power density is about 21.5 mW/cm² to about 22.5 mW/cm². In further embodiments, the UV power density is about 22 mW/cm².

In some embodiments, the substrate comprises at least one of: poly(ethylene terephthalate), polystyrene, polyethylene, or poly(methyl methacrylate). In further embodiments, the substrate comprises polystyrene. In some embodiments, the monomer solution is about 7% to about 12% diallyldimethyl ammonium chloride by weight. In other embodiments, the monomer solution is about 8% to about 10% diallyldimethyl ammonium chloride by weight. In additional embodiments, the photoinitiator is 2-Hydroxy-4'-(2-hydroxyethoxy)-2-methylpropiophenone. In some embodiments, the aqueous monomer solution additionally comprises an alcohol selected from the group consisting of: methanol, ethanol, propanol, and butanol. In further embodiments, the alcohol is ethanol.

In some embodiments, the water is purged of oxygen before the addition of the diallyldimethyl ammonium chloride, alcohol, and photoinitiator. In other embodiments, the water is purged by boiling and the addition of sodium periodate during boiling. In further embodiments, the water is allowed to cool to room temperature after boiling and before the addition of the diallyldimethyl ammonium chloride, alcohol, and photoinitiator.

In some embodiments, the substrate is plasma-treated prior to the UV-initiated polymerization reaction. In some embodiments, the substrate is cooled in an environment of about 10 degrees Celsius to about 15 degrees Celsius for about 30 seconds to about 30 minutes after being plasma-treated but prior to the UV-initiated polymerization reaction. In other embodiments, the substrate is cooled for about 5 minutes to about 15 minutes. In further embodiments, the substrate is cooled for about 10 minutes. In some embodiments, the device is concave on at least one side.

Another aspect of the disclosure herein includes for, in some embodiments, a method of manufacturing a device for selective capture of mycobacteria, the method comprising: providing a substrate; plasma treating the substrate to generate a plasma-treated substrate; providing an aqueous monomer solution comprising diallyldimethyl ammonium chloride and a photoinitiator in water purged of dissolved oxygen; and coating the plasma-treated substrate with a capture polymer layer of poly-diallyldimethyl ammonium chloride by applying the monomer solution to the plasma-treated substrate via a UV-initiated polymerization reaction, wherein the UV exposure time is about 30 seconds to about 4 minutes at a power density of about 20 to about 25 mW/cm². In some embodiments, the UV exposure time is about 50 seconds to about 1 minute and 10 seconds. In other embodiments, the UV exposure time is about 1 minute. In further embodiments, the UV exposure time is about 1 minute and 50 seconds to about 2 minute and 10 seconds. In additional embodiments, the UV exposure time is about 2 minutes. In some embodiments, the UV power density is about 22 to about 24 mW/cm². In other embodiments, the UV power density is about 21.5 mW/cm² to about 22.5 mW/cm². In further embodiments, the UV power density is about 22 mW/cm².

In some embodiments of the method, the substrate comprises polystyrene. In some embodiments, the plasma treatment is an oxygen plasma treatment. In some embodiments, the substrate is plasma treated for about 5 to about 15 minutes. In other embodiments, the substrate is plasma treated for about 9 minutes and 30 seconds to about 10 minutes and 30 seconds. In further embodiments, the substrate is plasma treated for about 10 minutes. In some embodiments, the substrate is plasma treated at an RF power setting of about 20 W to about 35 W. In other embodiments, the substrate is plasma treated at an RF power setting of about 29 W to about 30.2 W. In further embodiments, the substrate is plasma treated at an RF power setting of about 29.6 W.

In some embodiments, the method further comprises cooling the plasma-treated substrate in an environment of about 10 degrees Celsius to about 15 degrees Celsius for about 30 seconds to about 30 minutes. In other embodiments, the plasma-treated substrate is cooled for about 5 minutes to about 15 minutes. In further embodiments, the plasma-treated substrate is cooled for about 10 minutes.

In some embodiments of the method, the device is concave on at least one side. In some embodiments, the monomer solution is about 7% to about 12% diallyldimethyl ammonium chloride by weight. In other embodiments, the monomer solution is about 8% to about 10% diallyldimethyl ammonium chloride by weight. In some embodiments, the photoinitiator is 2-Hydroxy-4'-(2-hydroxyethoxy)-2-methylpropiophenone. In some embodiments, the aqueous monomer solution additionally comprises an alcohol selected from the group consisting of: methanol, ethanol, propanol, and butanol. In other embodiments, the alcohol is ethanol.

In some embodiments of the method, the water is purged of oxygen before the addition of the diallyldimethyl ammonium chloride, alcohol, and photoinitiator. In other embodiments, the water is purged by boiling and the addition of sodium periodate during boiling. In further embodiments, the water is allowed to cool to room temperature after boiling before the addition of the diallyldimethyl ammonium chloride, alcohol, and photoinitiator. In some embodiments, about 100 µL to about 500 µL of the monomer solution are applied to the plasma-treated substrate. In other embodiments, about 200 µL of the monomer solution are applied to the plasma-treated substrate. In further embodiments, about 400 µL of the monomer solution are applied to the plasma-treated substrate.

Another aspect of the disclosure herein includes for, in some embodiments, a method for selectively capturing mycobacteria comprising: incubating a prepared biological sample in a vessel comprising a mycobacteria capture device, the device comprising: a substrate coated with a capture polymer layer of poly-diallyldimethyl ammonium chloride, wherein the capture polymer layer is covalently linked onto the substrate via a UV-initiated polymerization reaction of an aqueous monomer solution comprising diallyldimethyl ammonium chloride and a photoinitiator in water purged of dissolved oxygen, and wherein the monomer solution is applied to the substrate and wherein the UV exposure time is from about 30 seconds to about 4 minutes at a power density of about 20 mW/cm² to about 25 mW/cm²; and centrifuging the vessel containing the sample so that the prepared biological sample is at least partially concentrated on the mycobacteria capture device.

In some embodiments of the method, the UV exposure time is about 50 seconds to about 1 minute and 10 seconds. In other embodiments, the UV exposure time is about 1 minute. In further embodiments, the UV exposure time is about 1 minute 50 seconds to about 2 minute 10 seconds. In additional embodiments, the UV exposure time is about 2 minutes. In some embodiments, the UV power density is about 22 mW/cm$^2$ to about 24 mW/cm$^2$. In other embodiments, the UV power density is about 21.5 mW/cm$^2$ to about 22.5 mW/cm$^2$. In further embodiments, the UV power density is about 22 mW/cm$^2$. In some embodiments, the monomer solution is about 7% to about 12% diallyldimethyl ammonium chloride by weight. In other embodiments, the monomer solution is about 8% to about 10% diallyldimethyl ammonium chloride by weight. In some embodiments, the device is concave on at least one side.

Another aspect of the disclosure herein includes for, in some embodiments, a kit for selectively capturing mycobacteria from a biological sample, the kit comprising: a vessel defining a cavity therein; a cap having an internal face, wherein the cap is adapted to seal the vessel; and a mycobacteria capture device comprising: a substrate coated with a capture polymer layer of poly-diallyldimethyl ammonium chloride, wherein the capture polymer layer is covalently linked onto the substrate via a UV-initiated polymerization reaction of an aqueous monomer solution comprising diallyldimethyl ammonium chloride and a photoinitiator in water purged of dissolved oxygen, and wherein the monomer solution is applied to the substrate and wherein the UV exposure time is about 30 seconds to about 4 minutes at a power density of about 20 mW/cm$^2$ to about 25 mW/cm$^2$; and wherein the mycobacteria capture device is adapted to removably couple to at least a portion of the internal face of the cap such that at least a portion of the mycobacteria capture device is exposed to the cavity defined by the vessel.

In some embodiments of the kit, the UV exposure time is about 50 seconds to about 1 minute and 10 seconds. In other embodiments, the UV exposure time is about 1 minute. In further embodiments, the UV exposure time is about 1 minute and 50 seconds to about 2 minutes and 10 seconds. In additional embodiments, the UV exposure time is about 2 minutes. In some embodiments, the UV power density is about 22 mW/cm$^2$ to about 24 mW/cm$^2$. In other embodiments, the UV power density is about 21.5 mW/cm$^2$ to about 22.5 mW/cm$^2$. In further embodiments, the UV power density is about 22 mW/cm$^2$. In some embodiments, the monomer solution is about 7% to about 12% diallyldimethyl ammonium chloride by weight. In other embodiments, the monomer solution is about 8% to about 10% diallyldimethyl ammonium chloride by weight. In some embodiments, the at least a portion of the mycobacteria capture device that is exposed to the cavity is concave.

Another aspect of the disclosure herein includes for, in some embodiments, a microfluidic chip for the selective capture of mycobacteria comprising: a substrate featuring a channel defined by at least one channel surface wall, the channel having a first and second opening; and wherein at least a portion of at least one channel surface wall is coated with a capture polymer layer of poly-diallyldimethyl ammonium chloride, wherein the capture polymer layer is covalently linked onto the substrate via a UV-initiated polymerization reaction of an aqueous monomer solution comprising diallyldimethyl ammonium chloride and a photoinitiator in water purged of dissolved oxygen, and wherein the monomer solution is applied to the substrate and wherein the UV exposure time is about 30 seconds to about 4 minutes at a power density of about 20 mW/cm$^2$ to about 25 mW/cm$^2$.

In some embodiments of the chip, the UV exposure time is about 50 seconds to about 1 minute and 10 seconds. In other embodiments, the UV exposure time is about 1 minute. In further embodiments, the UV exposure time is about 1 minute and 50 seconds to about 2 minutes and 10 seconds. In additional embodiments, the UV exposure time is about 2 minutes. In some embodiments, the UV intensity is about 22 mW/cm$^2$ to about 24 mW/cm$^2$. In other embodiments, the UV power density is about 21.5 mW/cm$^2$ to about 22.5 mW/cm$^2$. In additional embodiments, the UV power density is about 22 mW/cm$^2$. In some embodiments, the monomer solution is about 7% to about 12% diallyldimethyl ammonium chloride by weight. In other embodiments, the monomer solution is about 8% to about 10% diallyldimethyl ammonium chloride by weight.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

DETAILED DESCRIPTION

Figure 1A:
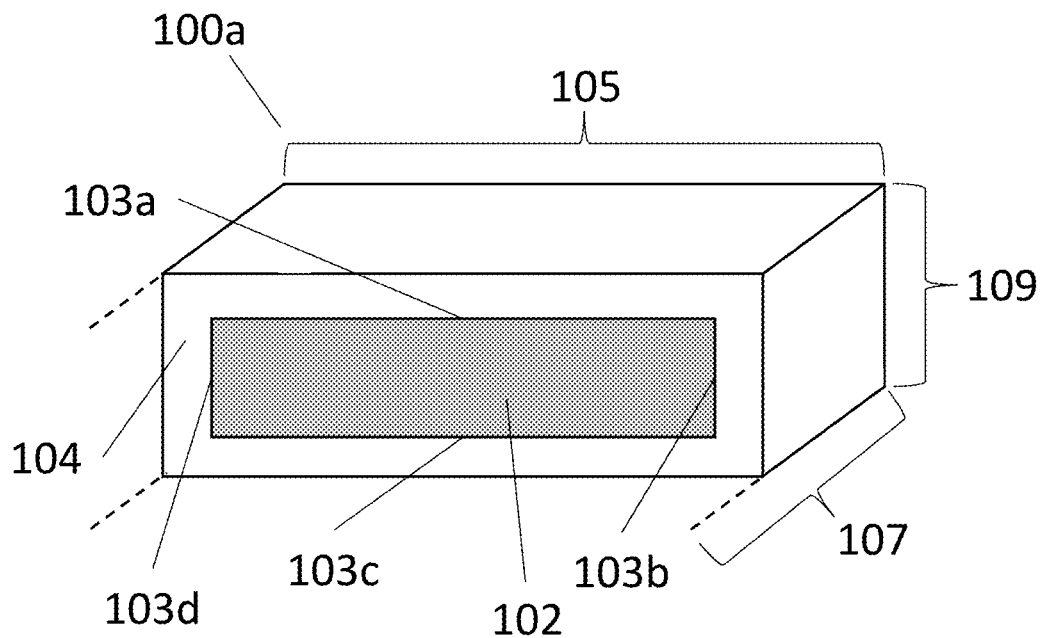
FIG. 1A illustrates a cross-sectional perspective view of one embodiment of a device for the selective capture of mycobacteria.

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Pathogenic mycobacteria are responsible for several severe infectious diseases in humans and animals. Mycobacteria are characterized by a hydrophobic, waxy coat comprising mycolic acid and related compounds. Mycolic acids are complex hydroxylated branched chain fatty acids, typically having hydrocarbon chains with a chain length in the range $C_{77}$-$C_{80}$. The waxy coat of pathogenic mycobacteria causes difficulties in sample handling.

Pathogenic mycobacteria include: *Mycobacterium tuberculosis*, which is the causative agent of TB; the mycobacteria of the *Mycobacterium avium* complex (MAC) (e.g., primarily *M. avium* and *M. intracellulare*), which are opportunistic pathogens in AIDS patients; *M. paratuberculosis*, which causes bowel inflammation; *M. leprae* causing leprosy; *M. kansasii*; *M. marinum*; *M. fortuitum* complex; and the like. Other non-pathogenic mycobacteria include *M. smegmatis*. Members of the Mycolata family also have similar hydrophobic waxy coats.

An inexpensive, simple, point-of-care diagnostic test for pulmonary tuberculosis has been highly sought after for years. The current state of the art involves the use of various sputum preparations on unmodified glass slides. This technique, however, suffers from a low sensitivity and is not able to diagnose pulmonary tuberculosis infections having a low bacterial count.

To diagnose mycobacterial infections, such as tuberculosis, the presence of the organism is determined by one of several diagnostic tests, including microscopy, culture, or molecular methods, such as polymerase chain reaction (PCR). Although microscopy can be done directly from the biological sample, the mycobacteria from the biological specimens are typically isolated and concentrated prior to analysis.

Biological samples containing or suspected of pathogenic mycobacteria include sputum, urine, blood, bronchial lavage, and the like. One of the most common samples used for diagnosing TB is sputum. Sputum, however, presents unique problems for bacteriology. Sputum is heterogeneous in nature and can be bloody, purulent, and viscous. It also can be contaminated with other micro-organisms, for example, Pseudomonas.

Prior to analysis, sputum typically is thinned and decontaminated by various pre-treatments steps, which include the use of 0.25-0.5 M sodium hydroxide with or without N-acetyl L-cysteine, sodium dodecyl sulphate, oxalic acid, or trisodium phosphate. Treatment times can be about 20 minutes to about 120 minutes. Such treatments are designed to thin the sputum and kill the majority of contaminating organisms. Because mycobacteria have a thick waxy coat, they are more resistant to such treatments. Even so, it is estimated that up to 60% of *M. tuberculosis* are killed or rendered non-viable by this treatment. Further processing of the sample, such as centrifugation, can increase the time and cost of the diagnosis and further risk contaminating the sample or exposing the laboratory technician to the pathogen.

Accordingly, it would be beneficial to be able to selectively isolate the pathogenic mycobacteria directly from the biological sample and, in the process, removing some or all of the contaminating organisms without resorting to harsh chemical decontamination processes. Such a process also would enhance survival of the mycobacteria of interest and increase the sensitivity of the subsequent diagnostic test.

Previous methods have attempted to physically coat a polar polymer onto glass and allowing it to dry via polar interactions. This physical coating method, however, is not effective in retaining the polymer on the glass surface and for capturing bacteria, if any. In contrast, the presently disclosed subject matter demonstrates that covalent bonding is necessary to reliably capture mycobacteria to a solid surface. Accordingly, the presently disclosed methods provide high efficiency TB capture and retention.

Further, prior work using pDADMAC was not based on the unique characteristics of mycobacteria, but rather on the fact that it is cationic and readily available. The presently disclosed subject matter demonstrates, however, that systematic engineering and screening of various polymer structures is important for identifying the best device candidates for TB capture with greater sensitivity and specificity. Thus, other compounds based on the chemical properties identified herein also could have the ability to capture mycobacteria. More particularly, as provided in more detail herein below, an intermediate charge density and moderate hydrophobicity are characteristic of the optimized surfaces. When the polymer is hydrophilic, pDADMAC-grafting will not give good TB capturing efficiency.

In developing such a diagnostic test for TB and other mycobacteria for developing countries and regions, four critical criteria must be considered. The test must be: based on a low-cost platform since the disease is concentrated in low- and middle-income countries; capable of enriching MTb from sputum samples, thereby increasing detection sensitivity; self-contained to minimize risk of contamination and the number of transfers of sputum samples between containers to reduce the biohazard risk; and compatible with existing microscope technologies to reduce infrastructure requirements.

One goal of the presently disclosed subject matter is to improve the sensitivity of sputum microscopy, thereby allowing hundreds of thousands of additional new cases of tuberculosis to be diagnosed and referred for treatment each year. One target goal of the presently disclosed subject matter is to exceed the improvement made by fluorescence LED microscopy, which has recently been endorsed by the WHO but offers only a 5-6% increase in sensitivity with an additional requirement for procurement of new equipment (LED microscope). The presently disclosed methods could achieve such an impact with minimal disruption to current workflow, which enables the presently disclosed methods to be easily deployed and implemented.

Further, the presently disclosed methods provide increased bacterial recovery to improve diagnostic sensitivity without the high cost, additional equipment, and cumbersome procedures found in methods known in the art. The presently disclosed methods also can be combined with LED microscopy to further increase its detection sensitivity.

Accordingly, the presently disclosed subject matter provides a polymeric system for capturing mycobacteria, for example, tuberculosis bacteria, thereby permitting a more sensitive diagnosis of TB. More particularly, the presently disclosed subject matter provides slides or films modified with a polymer having an affinity for particular mycobacteria that can selectively bind the mycobacteria on a surface, thereby enriching the mycobacteria of interest present within a biological sample and improving the detection limit. Such devices and methods concentrate and/or further manipulate the organism, such as capturing and washing the mycobacteria to remove non-infecting organisms or contaminants or to capture and transfer the mycobacteria from one solution to another.

More particularly, the presently disclosed subject matter provides surface-grafted polycationic polymer chains having an affinity for mycobacteria. In some embodiments, the presently disclosed subject matter provides a series of polymer grafting compositions designed to mimic the structures of tuberculosis bacteria-specific dyes. The non-specific surface properties of charge and hydrophobicity of the cationic polymer can be optimized to distinguish mycobacteria from other organisms found within sputum. The presently disclosed polymer-grafted surfaces exhibit various degrees of mycobacterial affinity and can be used for bacterial enrichment and detection.

U.S. Patent Application Publication No. US2017/0067088 for CATIONIC POLYMER SYSTEMS FOR SELECTIVE BACTERIAL CAPTURE, to O'Brien-Coon et al., published Mar. 9, 2017, makes an effort to utilize pDADMAC in the capture of mycobacteria, however, it fails to appreciate or describe a variety of critical structural and procedural parameters that enable efficient and effective capture. The advantages of the present disclosure are described herein.

Devices

The device functions to capture mycobacteria from a biological sample. In some embodiments, the device is adapted to preferably select for various types of mycobacteria over other microorganisms in the sample. The device is used for medical diagnostics, particularly for cheap and rapid testing for tuberculosis in a patient but can additionally or alternatively be used for any suitable applications, clinical or otherwise. The device can be configured or adapted to function for any suitable scenario where the isolation of mycobacteria or other microorganisms is valuable.

FIG. 1A shows a cross-sectional view (not drawn to scale) of a first embodiment of a device 100a for the selective capture of mycobacteria. The device 100a comprises a substrate 102 coated with a capture polymer layer 104. In various embodiments, the substrate 102, such as a plastic disc, film, or slide, can comprise a variety of polymer materials including, but not limited to: poly(ethylene terephthalate) (PET), polystyrene (PS), polyethylene (PE), and poly(methyl methacrylate) (PMMA). In some embodiments, the substrate 102 comprises polystyrene. The substrate 102 can have dimensions of such a size to be compatible with efficient diagnostic lab operations (e.g., with the kit as described below) and with common light and LED fluorescence microscopes. Because the capture polymer layer 104 is comparably very thin, the substrate 102 defines the general shape and size of the device 100a for selective capture of mycobacteria. In the embodiment of FIG. 1A, the substrate 102 is in the shape of a rectangular prism having a length 105 (e.g., the device's longest dimension), a width 107, and a thickness 107. Furthermore, the embodiment of the device 100 of FIG. 1A has the capture polymer layer 104 coated on all sides (i.e., surfaces) 103a, 103b, 103c, and 103d (two terminal end sides not shown). In other embodiments, the capture polymer layer 104 need not be present on all portions of all sides 103a-103d of the substrate 102. In many embodiments, the capture polymer layer 104 is present (e.g., by a covalent linkage as described herein) on at least a portion of at least one side or surface of the substrate 102.

Figure 1B:
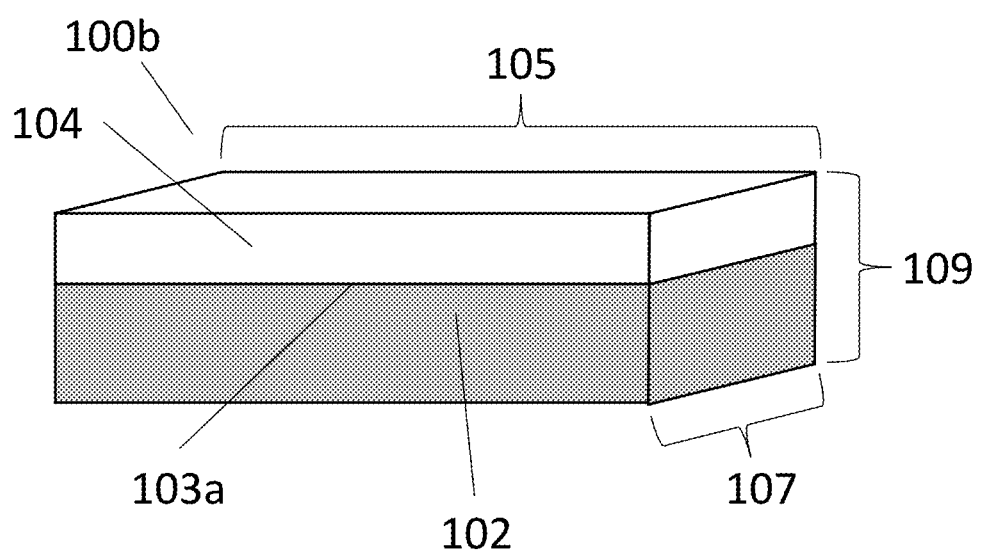
FIG. 1B illustrates a perspective view of a second embodiment of a device for the selective capture of mycobacteria.

FIG. 1B depicts a perspective view (not drawn to scale) of another embodiment of the device 100b wherein the capture polymer layer 104 is present only on a single side 103a of the substrate 102. Again, device 100b has the shape of a rectangular prism with a length 105 (i.e., the longest dimension of the device 100b), a width 107, and a thickness 109. In alternative embodiments, the capture polymer layer 104 can be present on additional sides or portions thereof of the substrate 102.

Figure 1C:
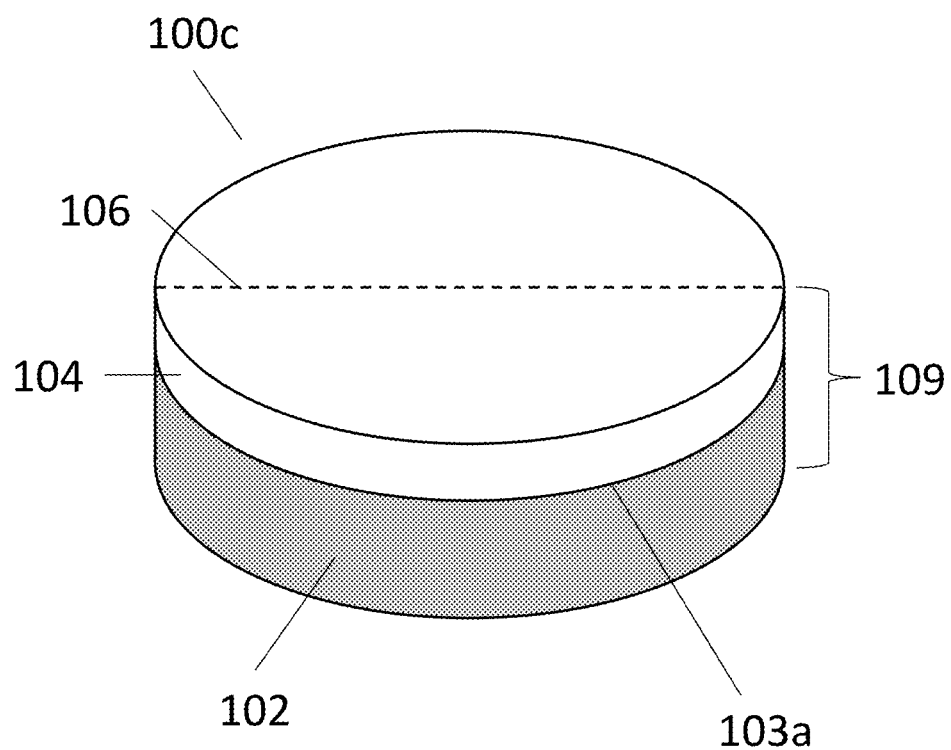
FIG. 1C illustrates a perspective of a third embodiment of a device for the selective capture of mycobacteria.

FIG. 1C depicts a perspective view (not drawn to scale) of another embodiment of the device 100c in the shape of a flat circular disc having a diameter 106 and a thickness 109. In this embodiment, the capture polymer layer 104 is present on only one side 103a of the substrate 102, although the capture polymer layer 104 can be present on additional sides or portions thereof of the substrate 102 in other embodiments.

Figure 1D:
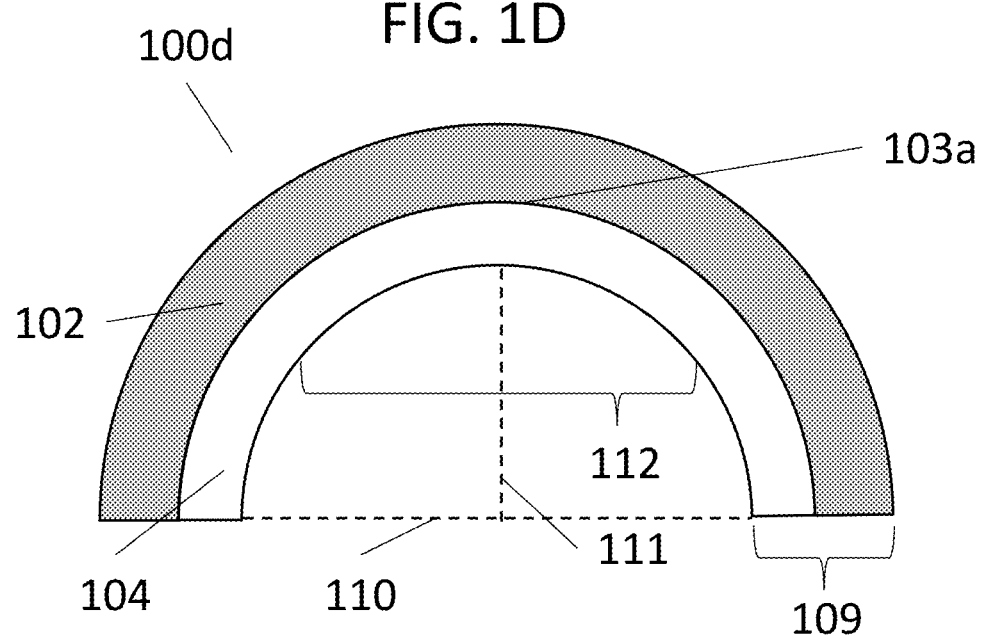
FIG. 1D illustrates a cross-section of a fourth embodiment of a device for the selective capture of mycobacteria.

FIG. 1D depicts a cross-sectional view (not drawn to scale) of another embodiment of the device 100d that takes the shape of a bowl (concave shape or surface) having a cavity diameter 110, a cavity depth 111, and a thickness 109. In this embodiment, the capture polymer layer 104 is present only on the concave side 103a, although in other embodiments, the capture polymer layer 104 can be present on additional sides or portions thereof of the substrate 102. Furthermore, in the embodiment of FIG. 1D, the cavity of the concave side 103a is shown to be semispherical; however, other curved geometries may also be used in alternative embodiments. The use of a concave side 103a in some embodiments can concentrate captured mycobacteria into a center region 112 under certain experimental and analytical conditions (see discussion of FIG. 3D below). The illustrations of FIGS. 1A-1D are not to scale and are not intended to depict exact dimensions or proportions of the device 100.

Across various embodiments, the device 100 can have any physical dimensions and any general shape, such as, but not limited to, that of a square or rectangular plate or a circular disc. In further embodiments, the device 100 can be a lab well plate coated with a capture polymer layer. In some embodiments, the device 100 can have a length 105 of about 1 mm to about 100 mm. In other embodiments, the device 100 can have a length 105 of about 1 mm to about 50 mm. In some embodiments, the device 100 can have a length 105 of about 1 mm to about 30 mm. In other embodiments, the device 100 can have a length 105 of about 1 mm to about 15 mm. In still other embodiments, the device 100 can have a length 105 of about 1 mm to about 10 mm. In further embodiments, the device 100 can have a length 105 of about 3 mm to about 12 mm.

In other embodiments, the device 100, can be a disc having a diameter 106 of about 1 mm to about 100 mm. In some embodiments, the device 100 has a diameter 106 of about 1 mm to about 50 mm. In some embodiments, the device 100 has a diameter 106 of about 1 mm to about 30 mm. In other embodiments, the device 100 has a diameter 106 of about 1 mm to about 15 mm. In still other embodiments, the device 100 has a diameter 106 of about 1 mm to about 10 mm. In further embodiments, the device 100 has a diameter 106 of about 3 mm to about 12 mm.

In some embodiments, the device 100 has a thickness 109 of about 0.01 mm to about 15 mm. In other embodiments, the device 100 has a thickness 109 of about 0.01 mm to about 1 mm. In still other embodiments, the device 100 has a thickness 109 of about 0.01 mm to about 5 mm. In further embodiments, the device 100 has a thickness 109 of about 0.1 mm to about 5 mm. In still further embodiments, the device 100 has a thickness 109 of about 0.1 mm to about 2.5 mm. In additional embodiments, the device 100 has a thickness 109 of about 0.5 mm to about 2.5 mm.

In many embodiments, the capture polymer layer 104 provides at least a substantial portion of the device's 100 ability to selectively capture mycobacteria by comprising a hydrophobic and polycationic polymer, the layer having additional structural properties described herein. In many embodiments, the polycationic polymer is poly-dimethyl-diallyl ammonium chloride (pDADMAC) shown below in Structure 1.

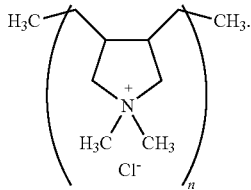

Structure 1

Figure 1E:
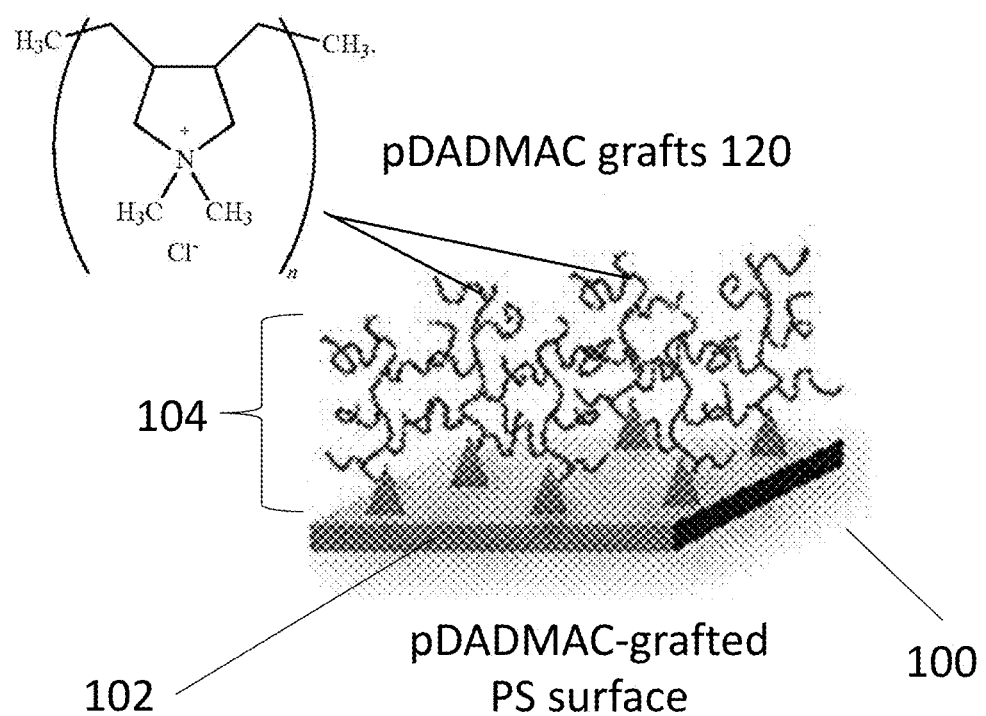
FIG. 1E depicts an illustration of pDADMAC grafts on a substrate surface.

FIG. 1E, depicting a schematic of the surface of the device 100 (not drawn to scale), depicts other properties of the capture polymer layer 104 that improve the device's selectivity for mycobacteria beyond those provided merely by pDADMAC's particular balance of hydrophobicity and positive charge density. In many embodiments, the capture polymer layer 104 comprises a packing of individual "brush-like" grafts 120 onto the substrate 102 with little cross-linking between them. This arrangement of individually attached grafts 106 with their exposed and flexible lengths of positively charged monomers can allow for the greater capture of mycobacteria in many embodiments compared to those having substantially cross-linked sheets of pDADMAC. Across many embodiments, these grafts can be generated by a carefully controlled UV-initiated free radical polymerization reaction having parameters and procedures, as described below in various embodiments.

Figure 2A:
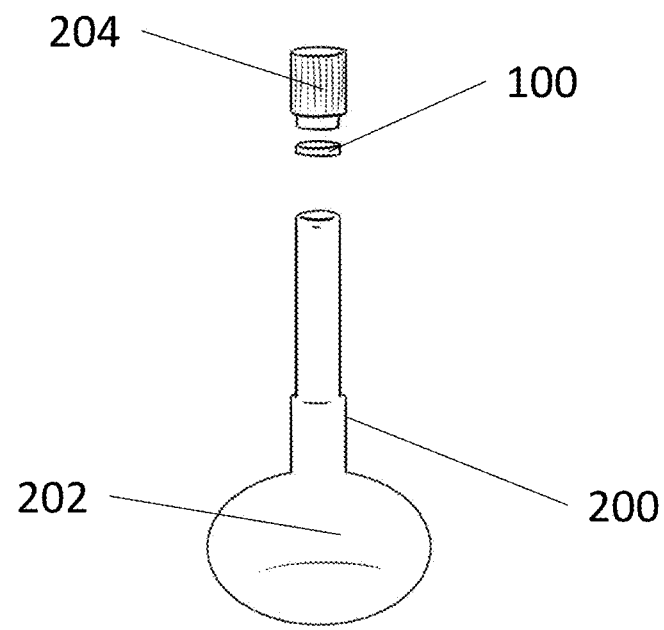
FIG. 2A illustrates an exploded view of one embodiment of a kit comprising a device for selective capture of mycobacteria.

As shown in FIG. 2A, the device 100 can be part of a kit 200 for selectively capturing mycobacteria in certain embodiments. The kit 200 can comprise a vessel 202 defining a cavity therein and a cap 204 for sealing the vessel 202. The device 100 comprising a substrate and a capture polymer layer (not shown) is adapted to be removably coupled to an interior face of the cap 204 such that at least a portion of the device 100 is exposed to the cavity of the vessel 202 when the device 100 and cap 204 is secured to the vessel 202. The vessel 202 can comprise any material suitable for medical diagnostics and the handling of biological materials, such as glass or various plastics as appreciated by those of skill in the art, and is adapted to receive a biological sample, including but not limited to a sputum sample, into its cavity. When sealed with the cap 204 having the device 100 disposed on an internal face of the cap 204, the kit 200 can then be centrifuged such that the force applies the biological sample to the exposed portion of the device 100 (e.g., in examples where the device 100 is secured within the cap 204 of the kit 200, the kit 200 is therefore centrifuged "upside-down" compared to normal usage of a centrifuge tube or Eppendorf tube). Due to the properties of the device 100 as described herein, mycobacteria can be selectively trapped in the capture polymer layer of the device 100. This method and related embodiments are discussed in greater detail below.

Figure 2B:
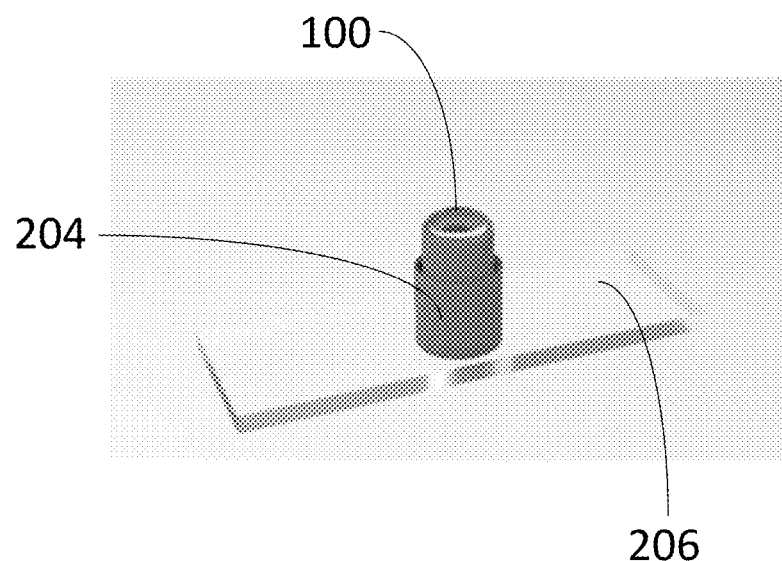
FIG. 2B illustrates an alternative view of a portion of a kit of FIG. 2A in use during medical diagnostics.

FIG. 2B shows the cap 204 of the kit 200 having the device 100 disposed thereon place on a slide 206 for further processing. Such an arrangement presents the device 100 to various lab equipment, such as but not limited to light and fluorescence LED microscopes, while being easy to handle about a laboratory space. In alternative embodiments, the device 100 is fully removed from the cap 204 and slide 206 and handled separately.

Figure 3A:
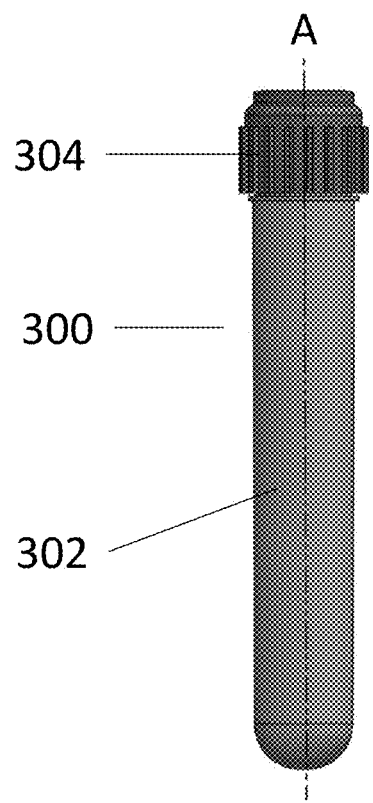
FIG. 3A illustrates an exterior view of one embodiment for a kit comprising a device for selective capture of mycobacteria.
Figure 3B:
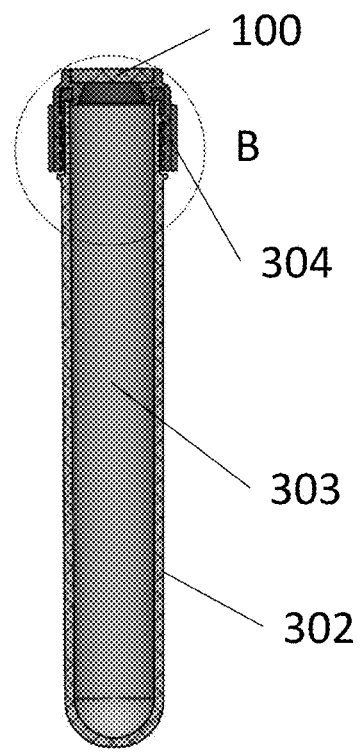
FIG. 3B illustrates a cross-sectional view of one embodiment of a kit comprising a device for selective capture of mycobacteria.
Figure 3C:
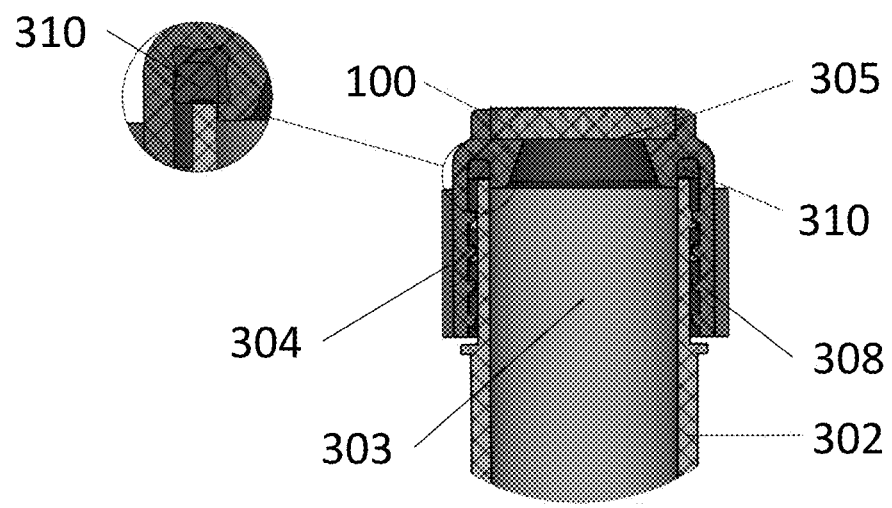
FIG. 3C illustrates a detailed view of a cross-section of a cap for one embodiment of a kit comprising a device for selective capture of mycobacteria.

FIG. 3A shows an alternative embodiment of a kit 300 featuring an embodiment of the device 100. The kit 300 can comprise a vessel 302 fitted with a cap 304. FIG. 3B shows a cross-section of FIG. 3A at Line A. In FIG. 3B, it can be seen that the vessel 302 defines a cavity 303 and the that cap 304 comprises the device 100. FIG. 3C shows a detailed view of the area of FIG. 3B defined by Circle B.

As shown in FIG. 3C, the cap 304 comprises the device 100 such that at least one surface 305 of the device 100 is exposed to the cavity 303 of the vessel 302. As described below in FIG. 6, this allows the kit 300 to be employed in a method of selectively capturing mycobacteria. When a sputum or other biological sample is placed within the cavity 303 and appropriately centrifuged (as described herein), the biological sample is therefore applied to the device 100 that will selectively capture mycobacteria over other microorganisms due to the properties and features of the device as described herein. In various embodiments, the cap 304 comprises an attaching mechanism 308 that allows the cap to be secured to the vessel 302. In the embodiment of FIG. 3C, a threaded groove configured to receive a corresponding thread of the vessel 302 is employed, although alternative fasteners (e.g., a snap-fit, a magnet, an adhesive, etc.) can be used in other embodiments. Furthermore, in some embodiments, the cap can feature an O-ring or other fitting 310 that can improve the seal between the cap 304 and the vessel 302 (fitting shown in further detail in insert). Additionally, the device 100 can be secured removably or irreversibly to the cap 304 by one or more physical mechanisms or chemical adhesive in various embodiments.

Figure 3D:
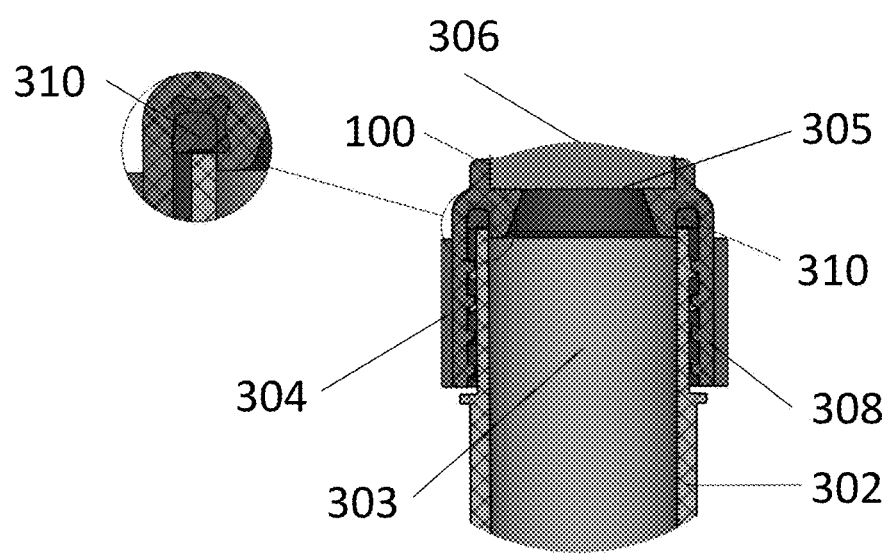
FIG. 3D illustrates a detailed view of a cross-section of a cap for another embodiment of a kit comprising a device for selective capture of mycobacteria.

FIG. 3D (not drawn to scale) shows a view similar to that of FIG. 3C but of an alternative embodiment. In this embodiment, the cap 304 comprises the device 100 such that at least one surface 305 of the device 100 is exposed to the cavity 303 of the vessel 302. As described below in FIG. 6, this allows the kit 300 to be employed in a method of selectively capturing mycobacteria. When a sputum sample is placed within the cavity 303 and appropriately centrifuged (as described herein), the biological sample is therefore applied to the device 100 that will selectively capture mycobacteria due to the properties and features of the device as described herein. Furthermore, the device 100 in the embodiment of FIG. 3D can have a shape such that at least one side of the device 100 (e.g., surface 305 of the device 100, side 103a of FIG. 1D, etc.) has a concave shape. When such a device is used in the method of FIG. 6, the concave shape of surface 305 directs the biological sample, including any mycobacteria contained within, into a center area or a substantially center area of the surface 305 (e.g., the center area 112 of side 103a of FIG. 1D). In certain embodiments, this can expedite subsequent analysis of the device as a user or piece of automated equipment need only then look at the center area 112 of the surface for captured mycobacteria instead of needing to search across the entire surface area, as can be required when employing a flat device 100 in some embodiments. This forced centralization of the captured mycobacteria also thus improves the limit of detection for many subsequent analyses, since all the mycobacteria are congregated into a smaller area (e.g., substantially central area versus entire surface area of the cap). This can even allow for the use of microscopy in the diagnosis of patients with typically low mycobacteria load, including children and HIV positive patients.

The curvature of the device 100 shown in FIG. 3D is not to actual scale, and the convex exterior surface 306 and flat interior surface 305 are meant to be merely illustrative of curvature of at least one side of the device 100 in some embodiments. In various embodiments, the cap 304 further comprises an attaching mechanism 308 that allows the cap to be secured to the vessel 302. In the embodiment of FIG. 3C, a threaded groove configured to receive a corresponding thread of the vessel 302 is employed, although alternative fasteners can be used in other embodiments. Furthermore, in some embodiments, the cap can feature an O-ring or other fitting 310 that can improve the seal between the cap 304 and the vessel 302 (fitting shown in further detail in insert.) Additionally, the device 100 can be secured removably or irremovably to the cap 304 by one or more physical mechanisms or chemical adhesive in various embodiments.

Figure 4:
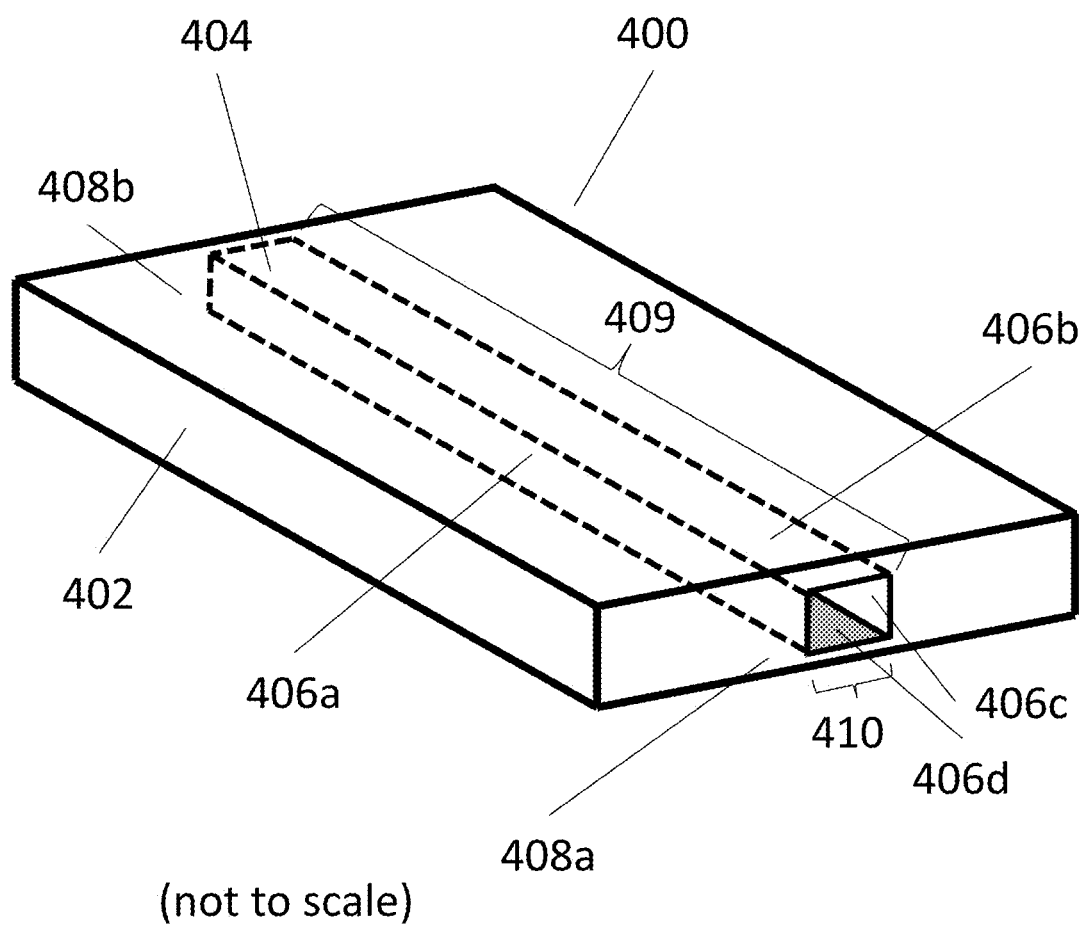
FIG. 4 illustrates a microfluidic chip for the selective capture of mycobacteria.

FIG. 4 depicts a microfluidic chip 400 that implements the capture polymer layer of the above figures as described herein for the selective capture of mycobacteria. The chip 400 can comprise a base substrate 402 through which runs a channel 404 (not to scale) defined by at least one channel surface walls (e.g., 406a, 406b, 306c, and 406d) running from a first opening 408a to a second opening 408b. In the embodiment of FIG. 4, the channel 402 has a square or rectangular cross-section defined by four channel surface walls 406a, 406b, 406c, and 406d. In other embodiments, the channel 404 can have a different cross-sectional shape defined by any number of channel surface walls including, but limited to, a triangle defined by three walls, and a circle or ellipse defined by one continuous channel surface wall.

In certain embodiments, the base substrate 402 comprises polydimethylsiloxane (PDMS). In other embodiments, the base substrate 402 comprises other materials known to those of skill in the art for the manufacturing of microfluidics chips. In some embodiments, the length 409 along the channel 404 from the first opening 408a to the second opening 408b can be from about 100 µm to about 1.0 mm. In other embodiments, the length 409 can be from about 250 µm to about 750 µm. In still other embodiments, the length 409 can be about 500 µm. In some embodiments, the width 410 of a given channel surface wall (e.g., 406d) across its surface perpendicular to its length from the first opening 408a to the second opening 408b can be from about 5 µm to about 50 µm. In other embodiments, the width 410 can be from about 10 µm to about 30 µm. In other embodiments, the width 410 can be about 20 µm. In some embodiments having a plurality of channel surface walls (e.g., the embodiment of FIG. 4), the plurality of channel surface walls (e.g., 406a, 406b, 406c, and 406d) can all have an equivalent width 410. In other embodiments having a plurality of channel surface walls, the channel surface walls 406a, 406b, 406c, and 406d can each have a different width 410. In still other embodiments, certain selections of the channel surface walls can have equivalent widths 410 while differing from other channel surface walls.

In many embodiments, at least a portion of at least one channel surface wall is coated in a capture polymer layer (e.g., in brush-like grafts of pDADMAC as described herein). In the embodiment of FIG. 4, the entire length of channel surface wall 406d is coated (shaded area). In other embodiments, the coating of the capture polymer layer is applied in a segmented or spotted pattern to one or more channel surface walls. In certain embodiments, all of the channel surface walls are coated with the capture polymer layer.

In this manner, various embodiments of the microfluidic chip 400 allow for the selective capture of mycobacteria. When a sample solution suspected of containing mycobacteria is provided to the first opening 408a of the chip 400 and a sufficient pressure-driven flow is supplied by a variety of microfluidic apparatuses as appreciated by those of skill in the art, the solution will pass through channel 404. As described above, mycobacteria will adhere and become trapped to the channel surface walls coated with the capture polymer layer (e.g., channel surface wall 406d of FIG. 3). Once the volume sample solution has passed through the channel 404, the microfluidic chip 400 can then be analyzed for the presence of mycobacteria by various techniques appreciated by those of skill in the art. The arrangement of the capture polymer layer onto a microfluidic chip as described herein thus allows for the selective capture of mycobacteria without the need for a centrifuge to spin down a sample and force suspected mycobacteria onto the device.

Methods

Figure 5:
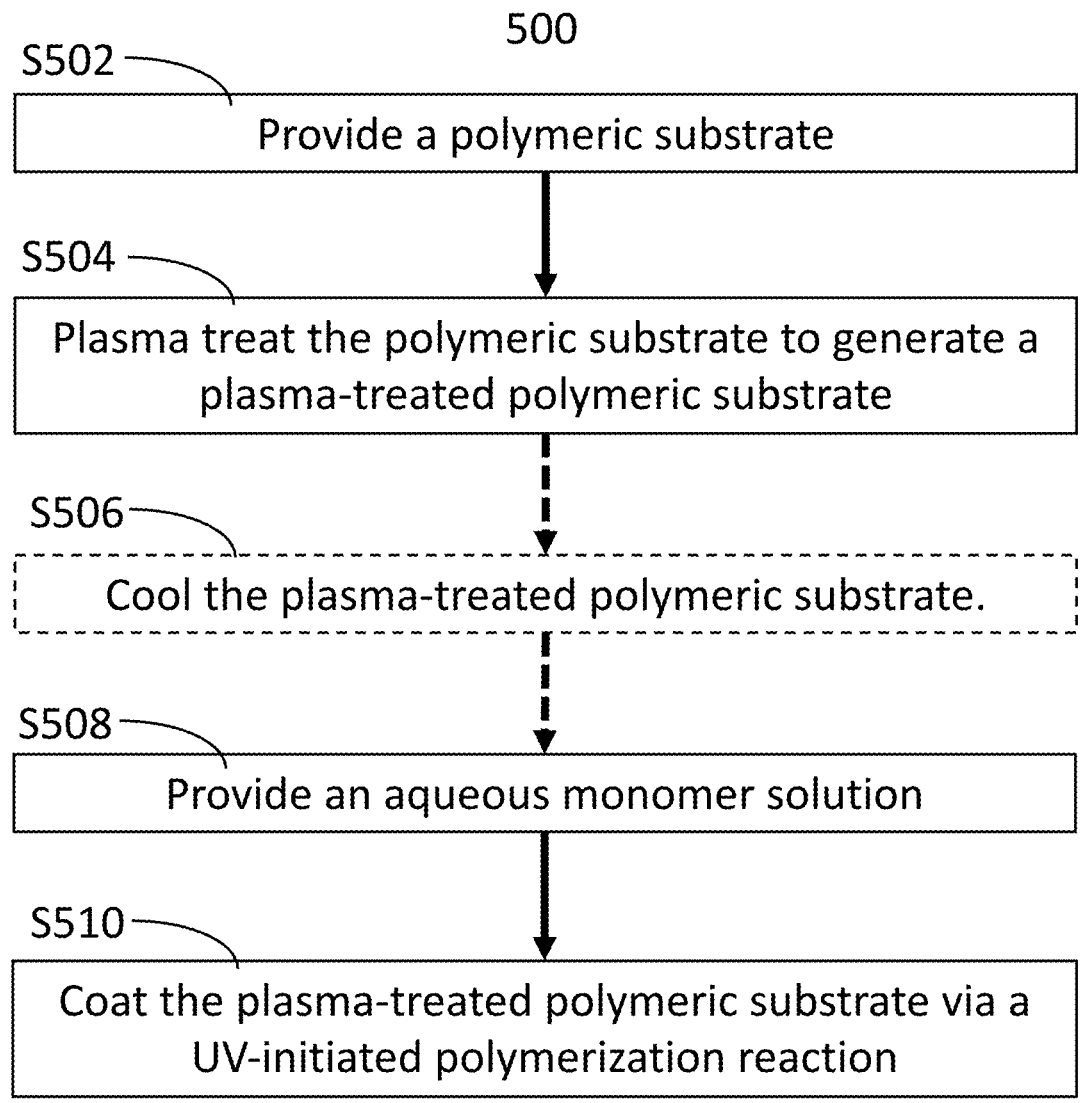
FIG. 5 illustrates a method of manufacturing a device for selective capture of mycobacteria.

FIG. 5 illustrates an embodiment of a method 500 for manufacturing a device for the selective capture of mycobacteria. As described above, particular manufacturing methods are required in order to consistently produce the "brush-like" grafts of FIG. 1B that demonstrate improved selectivity for the capture of mycobacteria over even previous work that employs pDADMAC as a capture polymer layer. In various embodiments, the method 500 allows for a substantially even distribution of brush-like grafts across a substrate regardless of the dimensions the substrate. In other embodiments, the quantities of the reactants can be scaled accordingly while preserving their molar or weight ratios in order to coat substrates of varying sizes. In one embodiment, the method 500 includes for providing a substrate in S502; plasma treating the substrate to generate a plasma-treated substrate in S504; optionally cooling the plasma-treated substrate in S506; providing an aqueous monomer solution in S508; and coating the plasma-treated substrate via a UV-initiated polymerization reaction in S510.

In one embodiment, the method 500 includes for providing a substrate in S502. The substrate can comprise a variety of polymer materials including, but not limited to: poly(ethylene terephthalate) (PET), polystyrene (PS), polyethylene (PE), and poly(methyl methacrylate) (PMMA). In some embodiments, the substrate comprises polystyrene. The substrate can have dimensions of such a size as to be compatible with efficient diagnostic lab operations (e.g., with the kit as described herein) and with common light and LED fluorescence microscopes. In some embodiments, the substrate can be a small disc, film, or slide, but one of skill in the art will appreciate that the substrate can take on a variety of sizes and shapes without departing from this disclosure. Similarly, the substrate can be made by a variety of methods known to those of skill in the art without departing from this disclosure.

In S504, an embodiment of the method 500 includes for plasma treating the substrate to generate a plasma-treated substrate. In various embodiments, the plasma treatment can involve the use of oxygen, nitrogen, hydrogen, argon, tetrafluoromethane gas, or a combination thereof. In many embodiments, the substrate is plasma treated with an oxygen plasma from oxygen gas. In addition to cleaning the substrate of any contaminants, plasma treating the substrate functionalizes the surface of the substrate with oxygen-based groups, which can include hydroxyls, carboxylic acids, epoxides, and oxygen radical groups in various embodiments. In many embodiments, this functionalization of the surface provides the attachment points for the grafts of the capture polymer layer. In certain embodiments, the substrate is plasma treated for 5 to 15 minutes at RF power setting of about 29.6 W (a setting of "high"), using oxygen gas supply with a Harrick Plasma cleaner. In other embodiments, a power setting of about 20 W to about 35 W can be used. In further embodiments, an RF power setting of about 29 W to about 30.2 W can be used. In further embodiments, the substrate is treated for about 9 minutes and 30 seconds to about 10 minutes and 30 seconds. In still other embodiments, the substrate is treated for about 10 minutes. One of skill in the art that a variety of devices can be used to perform this step. In some embodiments, the plasma-treated substrate is allowed to sit in the chamber of the plasma treater for less than or equal to about 30 minutes after plasma treatment (hereinafter, "time after plasma"). In other embodiments, the plasma-treated substrate is allowed to sit in the chamber of the plasma treater for about 30 seconds to about 15 minutes after plasma treatment. In further embodiments, the plasma-treated substrate is allowed to sit in the chamber of the plasma treater for about 5 minutes to about 10 minutes.

In some embodiments, the method 500 optionally includes for cooling the plasma-treated substrate in S506. In some embodiments, the plasma-treated substrate is cooled in an environment of about 0 degrees Celsius to about 20 degrees Celsius. In other embodiments, the plasma-treated substrate is cooled in an environment of about 10 degrees Celsius to about 15 degrees Celsius. Various techniques and apparatuses (e.g., a freezer or refrigerator, a cold-plate, etc.) can be employed to cool the plasma-treated substrate without deviating from the scope of this disclosure. In certain embodiments, the plasma-treated substrate is cooled by being placed on an ice bath (e.g., at about 10 degrees Celsius to about 15 degrees Celsius). In some embodiments, the plasma-treated substrate is cooled for about 30 seconds to about 30 minutes. In other embodiments, the plasma-treated substrate is cooled for about 5 minutes to about 15 minutes. In further embodiments, the plasma-treated substrate is cooled for about 10 minutes.

As discussed in Example 7 and FIG. 10 below, cooling the substrate following plasma treatment encourages the formation of favorable short brush-like grafts instead of long polymer chains during subsequent reactions as described herein. In this way, example devices constructed in this way report higher absorbance readings corresponding to a greater quantity of captured mycobacteria (see Example 7 below for further discussion).

Next, the method 500 includes providing an aqueous monomer solution at S508. In some embodiments, the aqueous monomer solution comprises monomeric DADMAC and a photoinitiator. In some embodiments, the monomeric solution is about 8% to about 20% by volume an aqueous solution of monomeric DADMAC that is itself about 50% to about 75% DADMAC by weight. In other embodiments, the monomeric solution is about 10% to about 15% by volume an aqueous solution of monomeric DADMAC that is itself about 50% to about 75% DADMAC by weight. In further embodiments, the monomeric solution is about 10% to about 15% by volume an aqueous solution of monomeric DADMAC that is itself about 65% DADMAC by weight. In still further embodiments, the monomeric solution is about 130.8% by volume an aqueous solution of monomeric DADMAC that is itself about 65% DADMAC by weight. In some embodiments, the monomeric solution is about 7% to about 12% DADMAC by weight. In other embodiments, the monomeric solution is about 8% to about 110% DADMAC by weight. In still other embodiments, the monomeric solution is about 8% to about 10% DADMAC by weight. In further embodiments, the monomeric solution is about 9% DADMAC by weight. In still further embodiments, the monomeric solution is about 10% DADMAC by weight. In some embodiments, the monomeric solution is about 8.6% DADMAC by weight. In other embodiments, the monomeric solution is about 8.9% DADMAC by weight. In additional embodiments, the monomeric solution is about 9.5% DADMAC by weight. In still more embodiments, the monomeric solution is about 9.9% DADMAC by weight.

In some embodiments, the photoinitiator is 2-Hydroxy-4'-(2-hydroxyethoxy)-2-methylpropiophenone, though one of skill in the art will appreciate that other photoinitiators can be used (including, but not limited to, Norish type I and type II photoinitiators, e.g., 2,2-Dimethoxy-1,2-diphenylethan-1-one, benzophenone, isopropyl thioxanthone, ethyl-4-(dimethylamino)benzoate, 2,3-bornanedione, etc.). In some embodiments, the aqueous monomer solution can additionally comprise an alcohol to improve the solubility of certain photoinitiators such as 2-Hydroxy-4'-(2-hydroxyethoxy)-2-methylpropiophenone. In these embodiments, the alcohol can be one or more selected from the group consisting of: methanol, ethanol, propanol, and butanol. In some embodiments, the alcohol is ethanol. In some embodiments, the volume ratio between water and the alcohol is about 1:1. In other embodiments, the water:alcohol volume ratio can be from about 10:1 to about 1:10. In further embodiments, the water:alcohol volume ratio can be from about 5:1 to about 1:5. In many embodiments, deionized water is used as the solvent for the aqueous monomer solution.

Because an abundance of oxygen free radicals in solution can interfere with the subsequent UV-initiated polymerization reaction, it can be valuable to purge the water solvent of such oxygen radical species before the addition of the above components in various embodiments. In some embodiments, this purging includes boiling the water. In further embodiments, the water is boiled in the presence of dissolved sodium periodate at a concentration of about 1 g/L, which assists in the expelling of oxygen radicals. In many embodiments, the water is allowed to cool to room temperature before the addition of the other components. See Example 1 herein for an exemplary procedure for making an embodiment for the aqueous monomer solution.

The method 500 includes for coating the plasma-treated substrate via a UV-initiated polymerization reaction to attach a capture polymer layer in S510. This can comprise applying a volume of the aqueous monomer solution to the surface of the substrate and then subjecting the mixture to UV light at a certain power for a certain duration of time. In many embodiments a volume less than or equal to about 1 mL of the aqueous monomer solution is used to coat a substrate having the dimensions commensurate with the device of FIGS. 2A and 2B. In some embodiments, a volume of about 100 microliters to about 500 microliters is used to coat such a substrate. In other embodiments, a volume of about 400 microliters is used to coat such a substrate. In further embodiments, a volume of about 200 microliters is used to coat such a substrate.

In some embodiments, the UV source is applied at about 10 to about 30 mW/cm$^2$ for about thirty seconds to about 4 minutes. In other embodiments, the UV source is applied at about 20 to about 25 mW/cm$^2$ for about thirty seconds to about 4 minutes. In further embodiments, the UV source is applied at about 21 mW/cm$^2$ to about 24 mW/cm$^2$ for about thirty seconds to about 4 minutes. In still other embodiments, the UV source is applied at about 22 mW/cm$^2$ to about 24 mW/cm$^2$ for about thirty seconds to about 4 minutes. In still further embodiments, the UV source is applied at about 21.5 mW/cm$^2$ to about 22.5 mW/cm$^2$ for about thirty seconds to about 4 minutes. In further embodiments, the UV source is applied at about 22 mW/cm$^2$ to about 24 mW/cm$^2$ for about thirty seconds to about 2 minutes. In additional embodiments, the UV source is applied at about 22 mW/cm$^2$ to about 24 mW/cm$^2$ for about 50 seconds to about 1 minute and 10 seconds. In still further embodiments, the UV source is applied at about 22 mW/cm$^2$ for about 1 minute. In still other embodiments, the UV source is applied at about 22 mW/cm$^2$ to about 24 mW/cm$^2$ for about 1 minute and 50 seconds to about 2 minutes and 10 seconds. In still further embodiments, the UV source is applied at about 22 mW/cm$^2$ for about 2 minutes. In still additional embodiments, the UV source is applied at about 21.5 mW/cm$^2$ to about 22.5 mW/cm$^2$.

Across various embodiments, it can be important to control the temperature of the solution during UV exposure. During UV exposure, new free radicals of the photoinitiator and therefore DADMAC are produced, and it is these DADMAC radicals that are capable of grafting onto the functionalized surface of the substrate. Additionally, higher temperatures increase the rate of polymerization among DADMAC. Therefore, if the temperature is too high and the population of DADMAC radicals are too few, only a small number of very long grafts will form. Conversely, if too many free radicals are generated in too cool of a temperature, only very short grafts will form with many likely cross-linkages. Therefore, in many embodiments, the parameters of UV power, duration, temperature of the reaction conditions, and quantity of both the monomeric DADMAC and photoinitiator are carefully balanced. In some embodiments, the reaction can be maintained at about 45° C. In some embodiments, including those applying UV light at about 22 mW/cm$^2$ to about 24 mW/cm$^2$ for about 1 to 2 minutes with a Dymax® 5000-EC UV treatment system, the UV source administers sufficient heat over the duration of the exposure that no additional heat monitoring or maintenance equipment is needed. In this manner, the technical problem of balancing the necessary heat of the reaction can be solved with the specific application of the power and/or duration of UV light which is already a necessary component of the desired reaction, thereby avoiding further complexity that adding additional apparatuses (such as heaters or coolers) may introduce.

After UV exposure, the devices can be washed with deionized water to remove any unreacted an excess aqueous monomer solution in some embodiments before being dried by any means appreciated by those of skill in the art. In certain embodiments, the devices are air-dried. Once the devices are dry, they can be used for in diagnostic tests to selectively capture mycobacteria such as described below in FIG. 6, packaged in a kit such as that of FIGS. 2A-3D, or used in any other manner.

Figure 6:
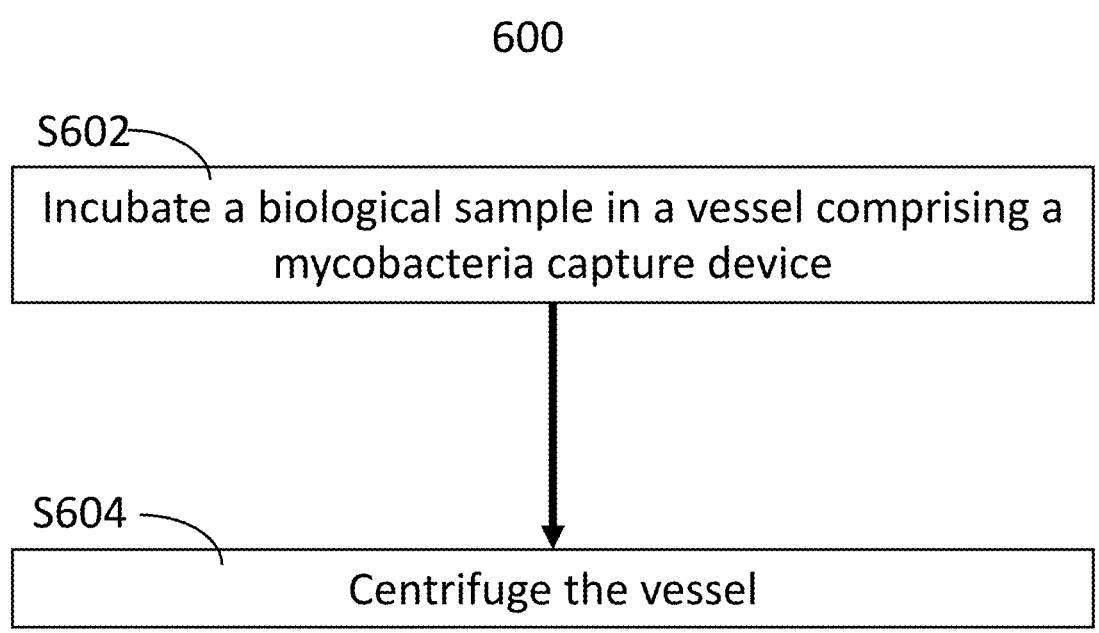
FIG. 6 illustrates a method of selectively capturing mycobacteria.

FIG. 6 illustrates one embodiment of a method 600 for selectively capturing mycobacteria. The method 600 can include incubating a biological sample in a vessel comprising a mycobacteria capture device in S602, and centrifuging the vessel in S604. In S602, the method 600 includes incubating a biological sample in a vessel comprising a mycobacteria capture device, such as the device of FIG. 1, integrated as part of a kit of FIGS. 2A-3D, and/or the device manufactured by the method of FIG. 5. In many embodiments, the biological sample is a sample that is suspected of containing mycobacteria. In some embodiments, the sample is a sputum sample. In many embodiments, incubating a biological sample within such a vessel can comprise the addition of various solvents and materials to appropriately prepare the sample before incubation. In certain embodiments, this can include the addition of water, dithiothreitol (DTT), and DNase.

At block S604, the method 600 includes centrifuging the vessel containing the device such that the centrifugal force of the motion applies the sample to at least a portion of the device. In some embodiments, the centrifugal force can be about 250 to about 5000 g. In other embodiments, the centrifugal force can be about 500 g. In other embodiments, the strength of the centrifugal force about 1000 g. In still other embodiments, centrifugal force can be about 3000 g. In further embodiments, the duration of the centrifugation can be about 3 minutes to about 15 minutes. In certain embodiments, the duration for the centrifugation can be about 10 minutes. Following the centrifugation of the vessel containing the device, the device can be removed for analysis. One of skill in the art will appreciate the broad variety of analyses that can be performed on the mycobacteria capture device including but not limited to light and LED fluorescence microscopy following a staining of the device. One of skill in the art will appreciate the variety of stains available for performing this task, including but not limited to Auramine.

Figure 7:
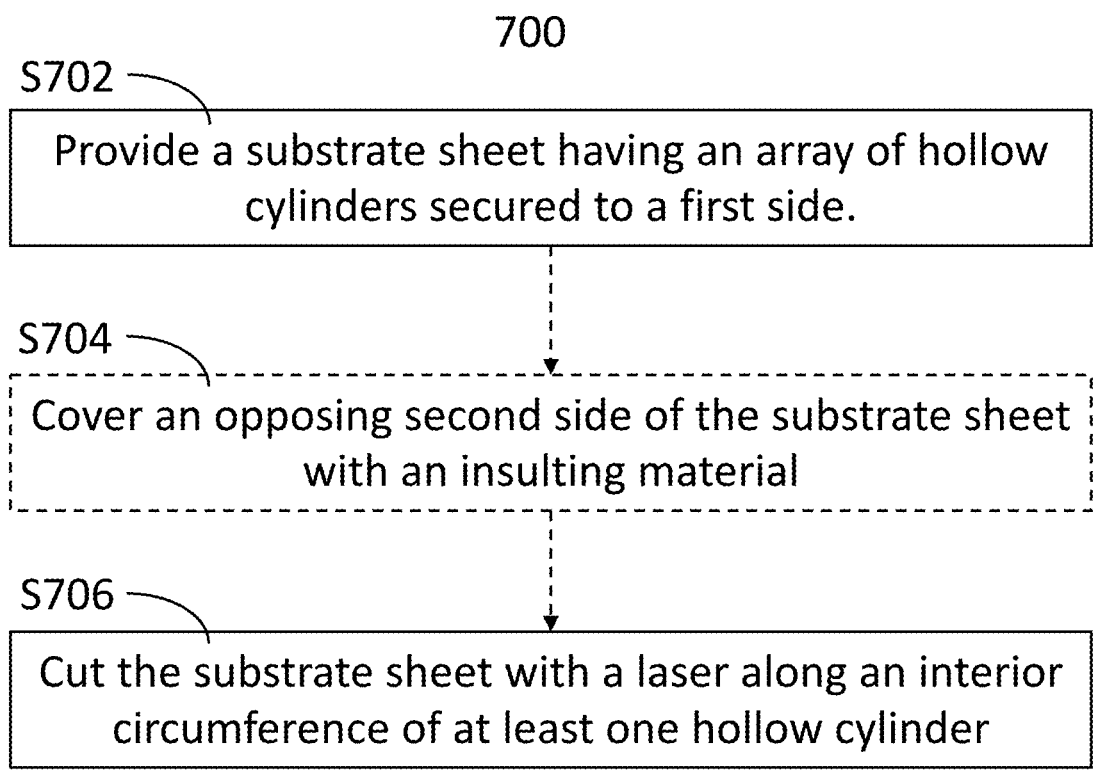
FIG. 7 illustrates a method of cutting a substrate to have a concave shape on one side.
Figure 8:
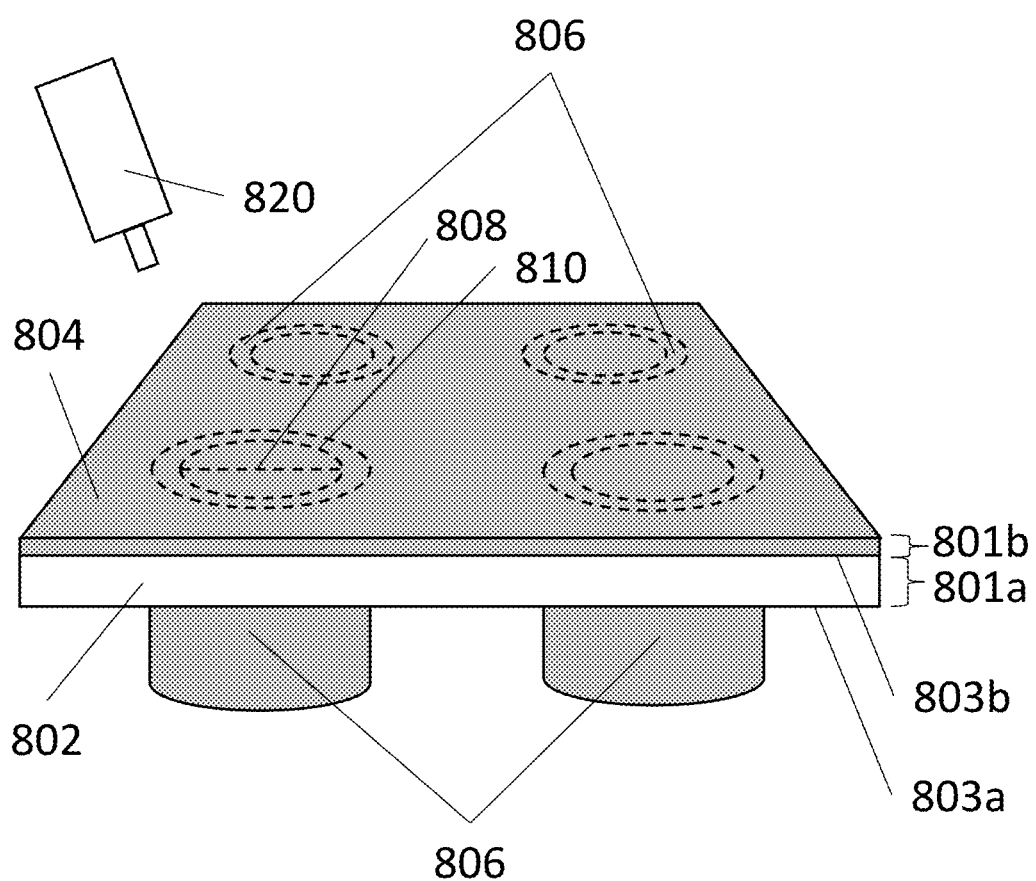
FIG. 8 illustrates an embodiment of an arrangement of materials to be cut in the production of a substrate having a concave shape on one side.

As described herein in certain embodiments, the mycobacterial capture device has a concave shape on at least one side (e.g. FIGS. 1D and 3D). FIG. 7 depicts an embodiment of a method 700 for manufacturing a disc having a concave shape on at least one side for use as a substrate as described herein. FIG. 8 depicts a perspective view of certain materials used in the method 700 before the act of cutting as described herein. The elements of FIG. 8 are not to scale, and the figure is intended to merely depict the relative orientation and identification of components only. An embodiment of the method 700 includes for providing a substrate sheet having an array of hollow cylinders secured to a first side in block S702, covering an opposing second side of the substrate sheet with an insulting material in block S704, and cutting the substrate sheet with a laser along an interior circumference of at least one hollow cylinder in block S706.

In some embodiments, the method 700 includes for providing a substrate sheet having an array of hollow cylinders secured to a first side in block S702. As shown in FIG. 8, the substrate sheet 802 has a thickness 801a. In many embodiments, the substrate sheet 802 comprises the material desired to be used as a substrate for a mycobacterial device as described herein (e.g., can comprise variety of polymer materials including, but not limited to: poly(ethylene terephthalate) (PET), polystyrene (PS), polyethylene (PE), and poly(methyl methacrylate) (PMMA)). Furthermore, the substrate sheet 802 can have a thickness 801a of about 0.1 mm to about 2.5 mm in various embodiments. In other embodiments, the substrate sheet 802 can have a thickness 801a of about 1 mm.

At least one hollow cylinder 806 is secured to a first side 803a of the sheet 802. The hollow cylinders 806 have an interior diameter 808 and an interior circumference 810 and can be secured to the first side 803a by an adhesive. A broad variety of adhesives can be employed without deviating from the scope of this disclosure. In many embodiments, the at least one hollow cylinder 806 can comprise one or more various plastics that can be the same or a different material from that of the substrate sheet 802. In these embodiments wherein the hollow cylinders 806 comprise plastic, a plastic glue can be used as the adhesive. A plurality of hollow cylinders 806 in the array can be spaced with any distance between them. Furthermore, any selection of hollow cylinders 806 within an array of hollow cylinders 806 need not all have an equivalent interior diameter 808 or interior circumference 810. In many embodiments, the interior diameter 808 of the hollow cylinders 806 is approximately or exactly equivalent to a diameter of the desired substrate for a mycobacterial capture device. In some embodiments, the interior diameter 808 can be from about 1 mm to about 30 mm. In other embodiments, the interior diameter 808 can be from about 1 mm to about 15 mm. In further embodiments, the interior diameter 808 can be about 12 mm.

Returning to FIG. 7, the embodiment of the method 700 can optionally include for covering an opposing second side of the substrate sheet with an insulating material in block S704. As shown in FIG. 8, a layer of insulating material 804 is secured to a side 803b that is opposite the side 803a that features the array of hollow cylinders 806. In some embodiments, the insulating material 804 is an insulating tape (e.g., masking or painters tape.) In these embodiments, because the insulating material 804 is an insulating tape, the adhesive of the tape secures the insulating material 804 to the substrate sheet 802. The insulating material 804 has a thickness 801b. In some embodiments, the thickness 801b of the insulating material 804 is about 0.1 mm to about 1.5 mm. In other embodiments, the thickness 801b of the insulating material 804 is about 0.3 mm to about 1 mm. In other embodiments, the thickness 801b of the insulating material 804 is about 0.5 mm to about 0.8 mm. The secured at least one hollow cylinder 806 induce a hoop stress in the substrate sheet 802 along the circle of contact where the hollow cylinder 806 touches the substrate sheet 802. As described herein, this hoop stress contributes to the deformation of the substrate sheet 802 during cutting that results in a device that has a concave shape on at least one side.

Returning to FIG. 7, the embodiment of the method 700 includes for cutting the substrate sheet with a laser along an interior circumference of at least one hollow cylinder in block S706. As shown in FIG. 8, a laser 820 positioned and aligned such that it can cut with its beam along the interior circumference 810 of at least one hollow cylinder 806 through the insulating material 804. Due to the heat of the laser 820 and the hoop stress applied to the substrate sheet 802 by the secured hollow cylinders 806, the cut discs deform during the cutting and subsequent cooling period to form a concave shape on at least one side of the disc. Alternative methods that do not generate heat or apply sufficient hoop stress (e.g., mechanical shearing or punching a flat sheet without secured cylinders 806) will result in flat discs as opposed to those with a concave shape on at least one side. Following the laser cutting, the insulating material 804 can be removed if desired.

In an alternative embodiment, the substrate sheet 802 can be cut along the interior circumference 810 by a mechanical tool, including, but not limited to, a knife or a hole punch. In these embodiments, the resulting disc can have a side or surface only slightly concave due to the hoop stress of the arrangement of the at least one secured cylinder 806 on the substrate sheet 802. Subsequently cutting the discs from these embodiments (having already insulated the disc's surface with an insulating material 804) with a laser to have a smaller diameter then provides sufficient heat that further deforms the disc, increasing its curvature. Following the laser cutting, the insulating material 804 can be removed if desired.

As used in the description and claims, the singular form "a", "an" and "the" include both singular and plural references unless the context clearly dictates otherwise. For example, the term "test" may include, and is contemplated to include, a plurality of tests. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 50%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

EXAMPLES

Example 1: Coating a PS Well Plate with pDADMAC (a First Embodiment)

For experimental purposes of testing the composition, a standard laboratory polystyrene well plate was acquired and plasma treated with low-temperature plasma for 10 minutes while the following aqueous monomer solution was prepared.

First, 100 mL of deionized water was brought to boil. At the peak of its boiling, 0.1 g of sodium periodate was added. The volume of water was then cooled by placing it in its container into a cold-water bath. Next, 5 mL of this freshly boiled water was then mixed with 5 mL of 100% ethanol before the addition of 0.5 g of IRGA 2959, i.e., as 2-Hydroxy-4'-(2-hydroxyethoxy)-2-methylpropiophenone. Finally, 1.6 mL of a 65% monomeric DADMAC solution by weight was added to this solution to yield the final aqueous monomer solution.

Then, 400 microliters of this solution was pipetted into each well of the plasma-treated well plate. The plates were then UV treated at about 22 mW/cm$^2$ for 1 minute. Following UV-treated, excess and/or unreacted aqueous monomer solution was washed away with deionized water, and the plate was air-dried.

Example 2: Efficacy Comparison 1

In order to test the efficacy of the method described herein against the methods of previous work, such as the work described in U.S. Patent Application Publication No. US2017/0067088 to O'Brien-Coon et al., which lacked the balance of photoinitiator, alcohol, temperature control, and used an about 2.5% to about 3% wt. DADMAC solution in place of the above solution of Example 1, the following side-by-side comparison was performed. Five well plates were prepared according to the procedure listed above in Example 1, except that the UV treatment time was varied for each plate. UV treatment times were 30 seconds, 1 minute, 2 minutes, 2.5 minutes, and 3 minutes, for the five plates. Five plates were prepared according to the procedure of U.S. Patent Application Publication No. US2017/0067088 to O'Brien-Coon et al. but had their UV treatment times similarly varied. A control plate and base plate were also prepared. In this example, the control plate undergoes the procedure but without any introduction of the monomeric DADMAC solution; the base plate is a well plate that has undergone no experimental operations or modifications. The absorbance of each plate was determined exposing each plate to a solution of acid orange 7 dye according to the following procedure.

1 mL of a solution of acid orange 7 dye (14 mg/mL) in DI water with pH adjusted to pH 3 using 1 M hydrochloric acid was placed in each well of the well plates. The plates were shaken on a plate shaker for 60 minutes before being washed with a pH 3 solution of hydrochloric acid to remove unbound dye and air dried. Once dry the plates were exposed to 1 mL of 0.25 M sodium carbonate (pH 11.25) and shaken on a lab shaker for 10 minutes. The average absorbance at 484 nm were calculated for the wells of the plates with a SpectraMax® i3X. Because acid orange 7 dye stains exposed pDADMAC, a higher absorbance reading indicates a greater quantity of pDADMAC bound to the surface, and therefore, a stronger selective capturer of mycobacteria in some embodiments.

Table 1 depicts the average absorbance and concentration of captured acid orange 7 dye of each protocol with that of the O'Brien Coon et al. disclosure listed as "Previous Work".

TABLE 1

| Polymer Protocol | UV Exposure Time (min) | Avg. Absorbance (A) | Concentration (g/L) |
|---|---|---|---|
| Present Disclosure | 0.5 | 0.067 | 0.02666879 |
| Previous Work | 0.5 | 0.056 | 0.022290332 |
| Present Disclosure | 1.0 | 0.14 | 0.055725829 |
| Previous Work | 1.0 | 0.053 | 0.021096207 |
| Present Disclosure | 2.0 | 0.072 | 0.028658998 |
| Previous Work | 2.0 | 0.074 | 0.029455081 |
| Present Disclosure | 2.5 | 0.402 | 0.160012737 |
| Previous Work | 2.5 | 0.125 | 0.049755204 |
| Present Disclosure | 3.0 | 0.091 | 0.036221789 |
| Previous Work | 3.0 | 0.134 | 0.053337579 |
| Control | — | 0.056 | 0.022290332 |
| Base | — | 0.032 | 0.012737332 |

In the majority of UV exposure times, the new method shows a marked improvement in quantity of pDADMAC over the previous work, most notably at the times of 1 minute and 2.5 minutes exposure times.

Example 3: Coating a PS Well Plate with pDADMAC (a Second Embodiment)

For experimental purposes of testing the composition, a standard laboratory polystyrene well plate was acquired and plasma treated with low-temperature plasma for 10 minutes and then chilled on an ice bath (approximately 10° C. to about 15° C.) for 10 minutes while the following aqueous monomer solution was prepared. In many embodiments, this cooling step is optional.

First, 100 mL of deionized water was brought to boil. At the peak of its boiling, 0.1 g of sodium periodate was added. The volume of water was then cooled by placing it in its container into a cold-water bath. Next, 5 mL of this freshly boiled water was then mixed with 5 mL of 100% ethanol before the addition of 0.5 g of IRGA 2959, i.e., as 2-Hydroxy-4'-(2-hydroxyethoxy)-2-methylpropiophenone. Finally, 1.6 mL of a 65% monomeric DADMAC solution by weight was added to this solution to yield the final aqueous monomer solution.

Then, 200 microliters of this solution was pipetted into each well of the plasma-treated well plate. The plates were then UV treated at about 22 mW/cm$^2$ for 2 minutes. Following UV-treated, excess and/or unreacted aqueous monomer solution was washed away with deionized water, and the plate was air-dried.

Example 4: Efficacy Comparison 2

Figure 9:
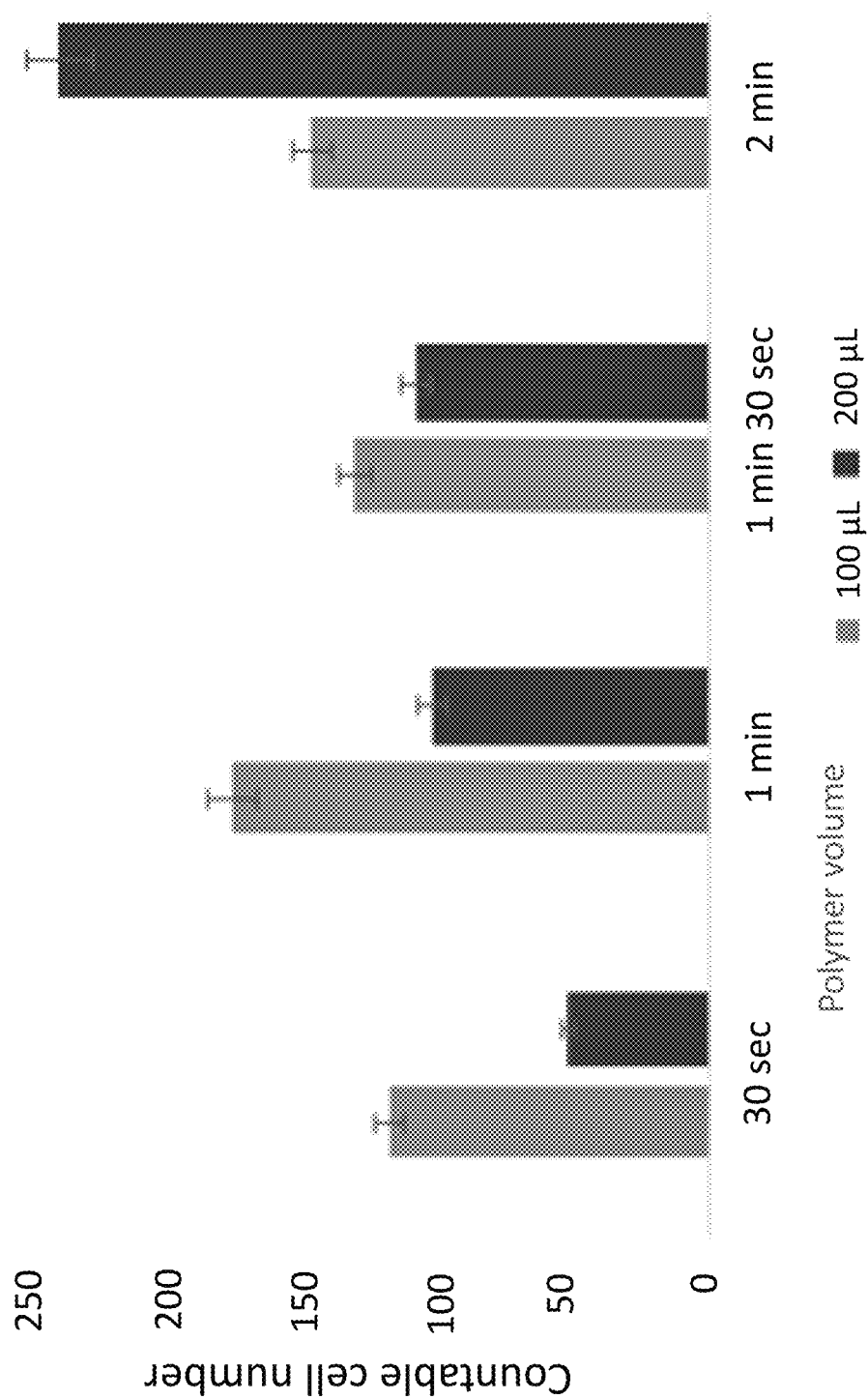
FIG. 9 illustrates data comparing the countable captured cells on different embodiments of the device.

FIG. 9 illustrates a comparison of the capture efficacy of various mycobacterial capture devices composed according to the embodiment of Example 3 but with variable UV exposure time (30 seconds, 1 minute, 1.5 minutes, and 2 minutes) and monomer solution volume (100 microliters or 200 microliters). All the example well plates (e.g., mycobacterial capture devices) of FIG. 7 forwent the optional cooling step and were immediately placed in the UV-initiated polymerization reaction upon plasma treatment. The plates were then exposed to a concentration of H37Ra bacilli ($9.6 \times 10^6$ CFU/mL) in DI water and centrifuged at 1000 g for 10 minutes. Next, the plates were washed three times with DI water and allowed to air dry before analysis by microscopy to count visible cells per field of view (about 194.94 μm×194.94 μm), calculating an average number of capture cells by each example well plate. The plate made with 200 μL of monomer solution under a 2-minute UV exposure time clearly outperformed all other examples, reaching nearly an average of 250 cells.

Example 5: Advantages of Coating—Distribution

Figure 10:
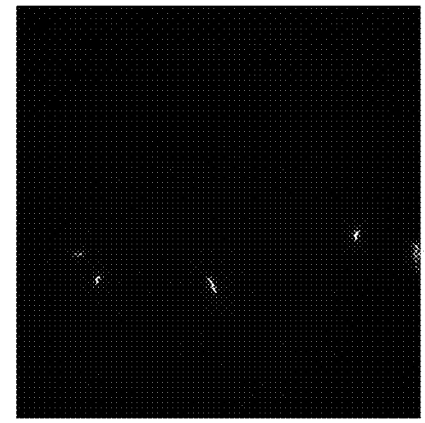
FIG. 10 illustrates images of captured cells on a device for selective capture of mycobacteria in comparison to an untreated polystyrene surface.
Figure 10:
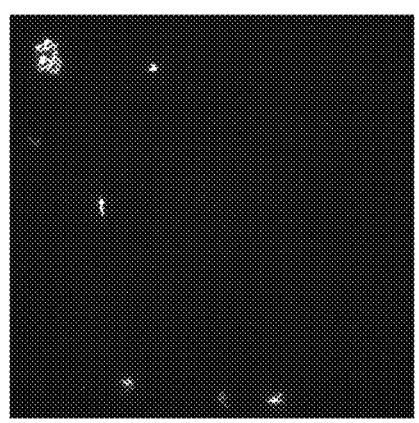
Figure 10:
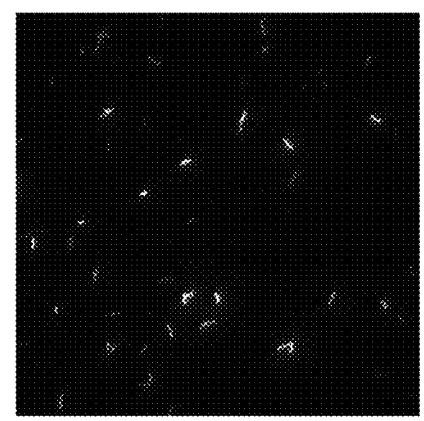
Figure 10:
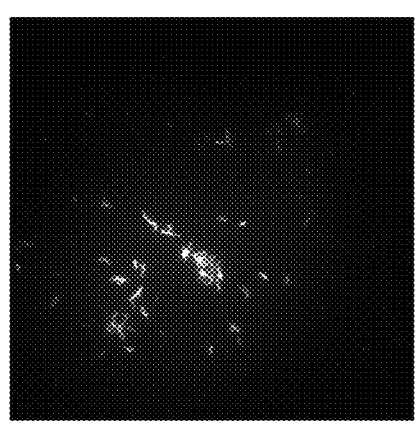
Figure 10:
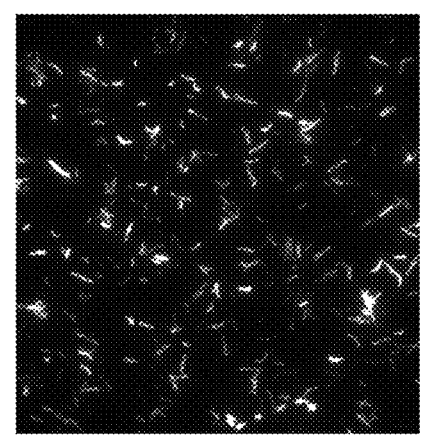
Figure 10:
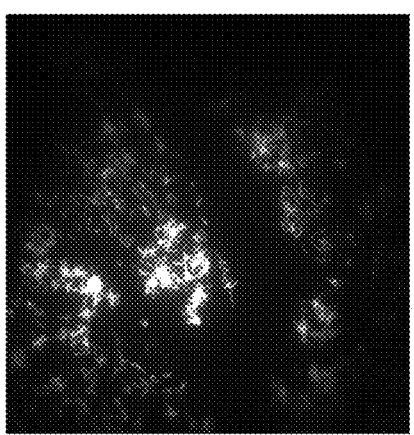

FIG. 10 depicts fluorescent microscopy images of fluorescent mycobacteria, provided at different concentrations, captured on both a device as described herein versus an unmodified polystyrene substrate. For each comparison, a mycobacterial capture device according to Example 1 and an untreated polystyrene well plate were exposed to an equivalent volume of a solution of H37Ra mycobacteria at concentrations of $10^5$ cells/mL, $10^4$ cells/mL, and $10^3$ cells/mL according to the procedure of Example 4 and allowed to air dry overnight. Images were collected at 600× magnification with a field of view of about 194.94 μm×194.94 μm. From these images, it can clearly be seen that the mycobacterial capture device allowed for a more even distribution of cells on its surface as opposed to the intense clustering seen in the untreated substrate. In many embodiments, the even distribution of the capture device is preferable as it facilitates individual cell counting in certain analyses.

Example 6: Advantages of Coating—Concentration

Figure 11:
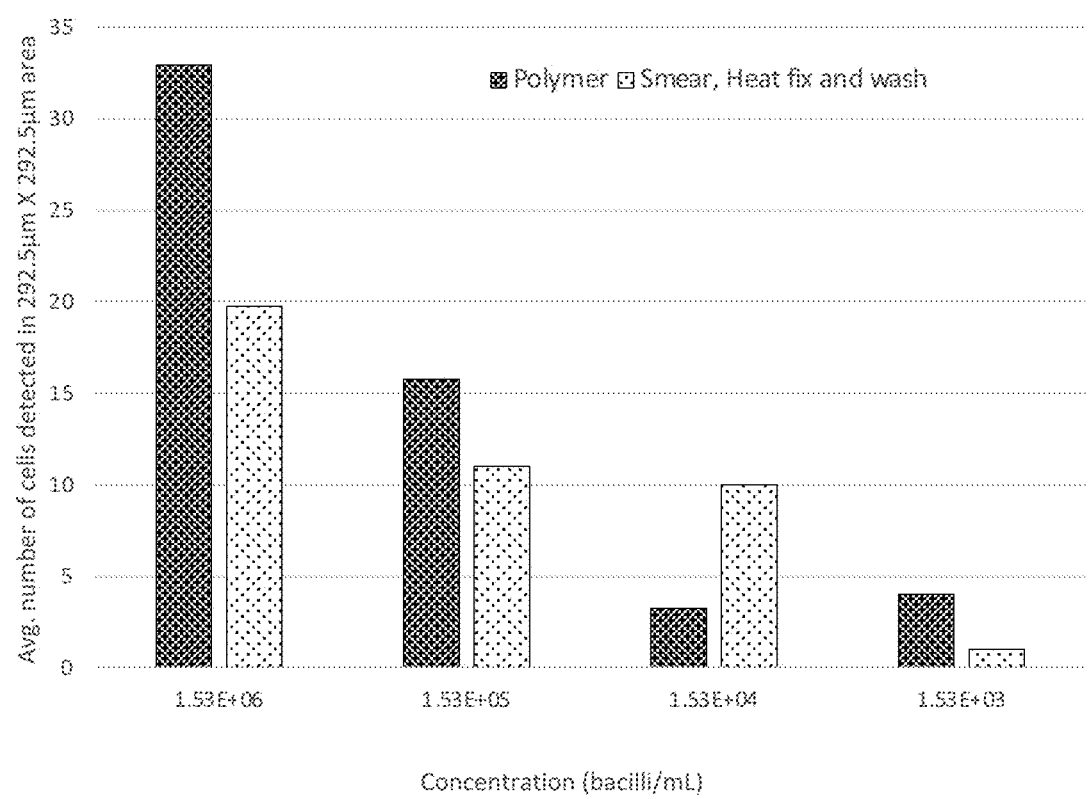
FIG. 11 illustrates data comparing the advantage of the device as described herein to preexisting capture methods.

FIG. 11 depicts results from a comparison of captured cells on a mycobacterial capture device as described herein versus a traditional heat smear preparation performed on an unmodified glass substrate. Mycobacterial capture devices were prepared according to the embodiment of Example 3 (including a 10-minute cooling period on an ice bath) and exposed to a solution of H37Ra mycobacteria of different concentrations ($1.53 \times 10^6$ bacilli/mL, $1.53 \times 10^5$ bacilli/mL, $1.53 \times 10^4$ bacilli/mL, and $1.53 \times 10^3$ bacilli/mL) according to the procedure of Example 4 Additionally, untreated glass substrates were exposed to the same sets of mycobacteria solutions by the traditional heat smear preparation as follows. The solutions were smeared onto the center of the substrate in an area of about 2 cm by 1 cm and allowed to air dry. Once dry, the smeared samples were then passed through the flame of a Bunsen burner three times. All samples were then analyzed by microscopy at 400× magnification to collect images at a field of view of about 292.5 μm by 292.5 μm area. An average quantity of cells present within this area was calculated from multiple images taken of each experimental parameter. Especially at highest and lowest concentrations of mycobacteria, the mycobacterial capture devices outperformed the traditional heat smear method by presenting a greater number of bacteria.

Example 7: Advantages of Cooling Following Plasma Treatment

Figure 12:
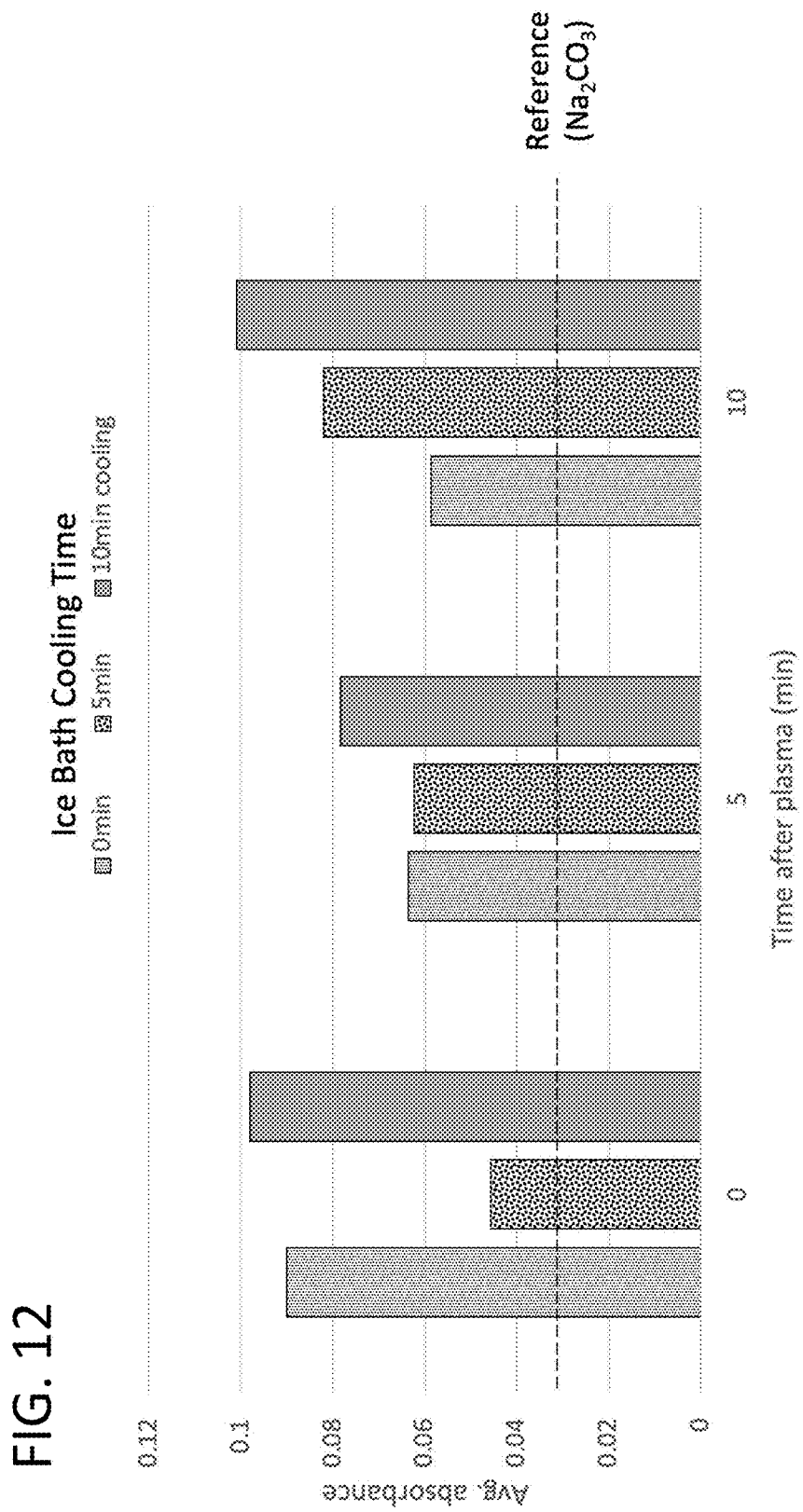
FIG. 12 illustrates data comparing the effect of a cooling period after plasma treatment on mycobacterial capture efficacy in various embodiments of the device for selective capture of mycobacteria; and The illustrated embodiments are merely examples and are not intended to limit the disclosure. The schematics are drawn to illustrate features and concepts and are not necessarily drawn to scale.

FIG. 12 illustrates the advantages of the cooling period with or without a "time after plasma" period following plasma treatment of the substrate. Mycobacterial capture devices were prepared according to the embodiment of Example 3 but given variable cooling times on an ice bath (i.e., about 10 degrees Celsius to about 15 degrees Celsius) and variable times after plasma before UV treatment. Next, acid orange 7 dye was applied to the plates as described above in Example 2 to measure the quantity of bound pDADMAC. A control of an untreated polystyrene well plate receiving only 1 mL of the sodium carbonate solution and shaken for 10 minutes was also prepared and measured.

Because acid orange 7 dye stains exposed pDADMAC, a higher absorbance reading indicates a greater quantity of pDADMAC bound to the surface, and therefore, a stronger selective capturer of mycobacteria in some embodiments. While all the tested devices outperformed the control, those with a 10-minute cooling period, with or without any time after plasma, generally reported a higher average absorbance indicative of a greater number of capture mycobacteria.

Example 8: Cutting of a Concave Disc

As discussed herein, certain embodiments of the device can benefit from being concave on at least one side of the device (e.g., FIGS. 1D and 3D, and FIGS. 7 and 8 depict an embodiment of a method for producing discs being concave on at least one side. In one example, a sheet of polystyrene having a thickness about 1 mm was lined with an insulating masking tape having a thickness of about 0.5 mm to about 0.8 mm across its top surface, thereby having a combined thickness of about 1.5 mm to about 1.8 mm. Next, an array of hollow plastic cylinders, each cylinder having an interior diameter of about 12 mm, was adhered with a glue to the side of the polystyrene sheet opposite the insulating tape. The adhered hollow cylinders induce a hoop stress in the sheet along the circle of contact where the cylinder touches the sheet. A laser cutter (e.g., a Universal® Laser Systems VSL3.50, etc.) operating with a hairline beam width (approximately 0.075 mm was then aligned and cut the polystyrene sheet through the insulating tape along the interior circumference of each cylinder. Due to the heat of the laser and the hoop stress generated on the sheet by the secured array of cylinders, the cut discs shrunk at the edge and deformed to have at least one side as concave as they cooled.

What is claimed is:

1. A method of manufacturing a device for selective capture of mycobacteria, the method comprising:
   providing a substrate;
   plasma treating the substrate to generate a plasma-treated substrate;
   providing an aqueous monomer solution comprising diallyldimethyl ammonium chloride and a photoinitiator in water purged of dissolved oxygen;
   covalently linking a capture polymer layer of poly-diallyldimethyl ammonium chloride to the plasma-treated substrate by applying the aqueous monomer solution to the plasma-treated substrate via a UV-initiated polymerization reaction,
   wherein a UV exposure time is about 30 seconds to about 4 minutes at a power density of about 20 mW/cm² to about 25 mW/cm²; and
   cooling the plasma-treated substrate to about 0 degrees Celsius to about 20 degrees Celsius.

2. The method of claim 1, wherein the plasma treating the substrate is with an oxygen plasma treatment.

3. The method of claim 1, wherein the plasma treating the substrate is for about 5 to about 15 minutes at an RF power setting of about 20 W to about 35 W.

4. The method of claim 1, wherein cooling the plasma-treated substrate is for about 30 seconds to about 30 minutes.

5. The method of claim 1, wherein the aqueous monomer solution is about 7% to about 12% diallyldimethyl ammonium chloride by weight.

6. The method of claim 1, wherein the photoinitiator is 2-Hydroxy-4'-(2-hydroxyethoxy)-2-methylpropiophenone.

7. The method of claim 1, wherein the aqueous monomer solution additionally comprises an alcohol selected from the group consisting of: methanol, ethanol, propanol, and butanol.

8. The method of claim 1, wherein the UV exposure time is about 50 seconds to about 1 minute and 10 seconds.

9. The method of claim 1, wherein the substrate comprises polystyrene.

10. The method of claim 1, wherein the substrate is a solid substrate.

11. The method of claim 1, wherein the aqueous monomer solution is about 8.9% diallyldimethyl ammonium chloride by weight.

12. The method of claim 1, wherein the aqueous monomer solution is about 8% to about 10% diallyldimethyl ammonium chloride by weight.

13. A method of manufacturing a device for selective capture of mycobacteria, the method comprising:
 providing a substrate;
 plasma treating the substrate to generate a plasma-treated substrate;
 providing an aqueous monomer solution comprising diallyldimethyl ammonium chloride and a photoinitiator;
 covalently linking a capture polymer layer of poly-diallyldimethyl ammonium chloride to the plasma-treated substrate by applying the aqueous monomer solution to the plasma-treated substrate via a UV-initiated polymerization reaction; and
 cooling the plasma-treated substrate to about 0 degrees Celsius to about 20 degrees Celsius for about 30 seconds to about 30 minutes.

14. The method of claim 13, wherein the plasma treating the substrate is with an oxygen plasma treatment.

15. The method of claim 13, wherein the plasma treating the substrate is for about 5 minutes to about 15 minutes.

16. The method of claim 15, wherein the plasma treating the substrate is at an RF power setting of about 20 W to about 35 W.

17. The method of claim 13, wherein the aqueous monomer solution is about 7% to about 12% diallyldimethyl ammonium chloride by weight.

18. The method of claim 13, wherein the photoinitiator is 2-Hydroxy-4'-(2-hydroxyethoxy)-2-methylpropiophenone.

19. The method of claim 13, wherein the aqueous monomer solution additionally comprises an alcohol selected from the group consisting of: methanol, ethanol, propanol, and butanol.

20. The method of claim 13, wherein a UV exposure time, for the UV-initiated polymerization reaction, is about 50 seconds to about 1 minute and 10 seconds.

21. The method of claim 13, wherein the substrate comprises polystyrene.

* * * * *